(12) United States Patent
Luo

(10) Patent No.: US 8,952,002 B2
(45) Date of Patent: Feb. 10, 2015

(54) AMINOHETEROARYL COMPOUNDS AND PREPARATION METHOD AND USE THEREOF

(71) Applicant: Huibing Luo, Shanghai (CN)

(72) Inventor: Huibing Luo, Shanghai (CN)

(73) Assignee: Shanghai Allist Pharmaceuticals, Inc. (CN)

( * ) Notice: Subject to any disclaimer, the term of this patent is extended or adjusted under 35 U.S.C. 154(b) by 0 days.

(21) Appl. No.: 14/372,295

(22) PCT Filed: Jan. 17, 2013

(86) PCT No.: PCT/CN2013/000044
§ 371 (c)(1),
(2) Date: Jul. 15, 2014

(87) PCT Pub. No.: WO2013/107285
PCT Pub. Date: Jul. 25, 2013

(65) Prior Publication Data
US 2014/0357613 A1    Dec. 4, 2014

(30) Foreign Application Priority Data

Jan. 17, 2012 (CN) .......................... 2012 1 0023327

(51) Int. Cl.
*A61K 31/00* (2006.01)
*C07D 401/00* (2006.01)
*C07D 401/14* (2006.01)

(52) U.S. Cl.
CPC ................................... *C07D 401/14* (2013.01)
USPC ..................................... 514/210.2; 546/268.4

(58) Field of Classification Search
None
See application file for complete search history.

(56) References Cited

FOREIGN PATENT DOCUMENTS

| WO | WO 2007/132308 A1 | 11/2007 |
| WO | WO 2008/008539 A2 | 1/2008 |
| WO | WO 2008/071451 A1 | 6/2008 |
| WO | WO 2009/099982 A1 | 8/2009 |

OTHER PUBLICATIONS

International Search Report corresponding to International Application No. PCT/CN2013/000044 mailed Apr. 25, 2013.
Written Opinion of the International Searching Authority corresponding to International Application No. PCT/CN2013/000044 mailed Apr. 25, 2013.
International Preliminary Report on Patentability corresponding to International Application No. PCT/CN2013/000044 issued Jul. 22, 2014.
Bottaro et al. "Identification of the Hepatocyte Growth Factor Receptor as the c-*met* Proto-Oncogene Product", *Science* 251:802-804 (1991).
Cecchi et al. "Targeting the HGF/Met signaling pathway in cancer", *Eur. J. Cancer* 46:1260-1270 (2010).
Christensen et al. "c-Met as a target for human cancer and characterization of inhibitors for therapeutic intervention", *Cancer Letters* 225:1-26 (2005).
Park et al. "Sequence of *MET* protooncogene cDNA has features characteristic of the tyrosine kinase family of growth-factor receptors", *Proc. Natl. Acad. Sci. USA* 84:6379-6383 (1987).
Porter "Small molecule c-Met kinase inhibitors: a review of recent patents", *Expert Opin. Ther. Patents* 20(2):159-177 (2010).

*Primary Examiner* — Heidi Reese
(74) *Attorney, Agent, or Firm* — Myers Bigel Sibley & Sajovec, P.A.

(57) ABSTRACT

The present invention refers to aminoheteroaryl compounds of the following formula (I) as well as the preparation method and use thereof, wherein $R^1$ and $R^3$ are defined in the Description in details. The aminoheteroaryl compounds of the present invention are inhibitors of hepatocyte growth factor receptor (c-Met), have favorable inhibitory effect against c-Met and inhibitory effect against the proliferation of cancer cells, such that they may be used as therapeutic agents for the treatment of tumors and related diseases.

(I)

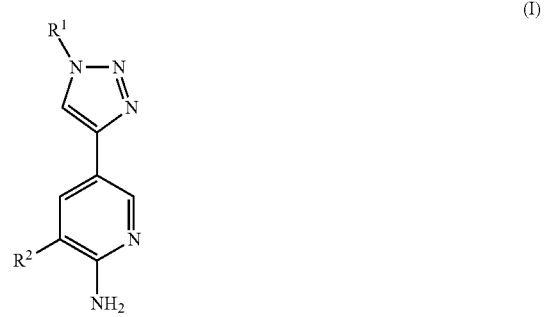

16 Claims, 2 Drawing Sheets

AMINOHETEROARYL COMPOUNDS AND PREPARATION METHOD AND USE THEREOF

RELATED APPLICATIONS

This application is a 35 U.S.C. §371 national phase application of PCT Application PCT/CN2013/000044 filed Jan. 17, 2013, which claims priority to CN 201210023327.1 filed Jan. 17, 2012. The entire content of each of these applications is incorporated herein by reference.

TECHNICAL FIELD

The present invention relates to aminoheteroaryl compounds that inhibit the activity of hepatocyte growth factor receptor (c-Met) and preparation method thereof, a pharmaceutical composition containing said compound and use of said compound in the prevention and/or treatment of c-Met mediated diseases and in the preparation of a medicament for the prevention and/or treatment of c-Met mediated meiwenti diseases.

BACKGROUND TECHNOLOGY

Cancer is one of the most fateful diseases that threaten human beings' lives and health. In various diseases, the mortality of malignant tumor is among the second place, just behind cardiovascular and cerebrovascular diseases. Although medical technologies are developing constantly, and the therapeutic means for cancer in which surgery as well as radiochemotherapy and chemoradiotherapy are selected as the major approaches have made great progress, however, cancer is still very difficult to treat since the pathogenesis thereof is complex. Consequently, finding the small molecule anticancer agents with high efficacy and low toxicity is always the hot spot and difficulty in the realm of current cancer treatment.

Hepatocyte growth factor receptor (c-Met) is a receptor type tyrosine kinase, which is encoded by Met proto-oncogene (Bottaro D P et al. Science 1991, 251(4995):802~804) and generally includes 190-kDa heterodimer (a 50-kDa α-chain and a 145-kDa β-chain linked by bisulfide) transmembrane tyrosine kinase protein (Proc. Natl. Acad. Sci. USA, 1987, 84:6379~6383). C-Met has the biological effect of transducting hepatocyte growth factor (HGF). As the ligand of c-Met, HGF is also known as scatter factor (SF), which is a heterodimer protein secreted by cells originated from mesoderm. C-Met and HGF are needed by the growth of normal mammals, expressed in the many tissues, and are shown to be important in cell migration, cellular proliferation and survival, morphogenesis and differentiation, as well as the organization of 3-dimensional tubiform structure (e.g. the formation of nephridia cells and glands) (James G. Christensen, et al., Cancer Letters, 2005, 225: 1~26). HGF induces the mitogenesia of epithelial cells, stimulates cell mobility and promotes the penetration of matrix. Besides the effect on epithelial cells, HGF/SF has also been reported to be an angiogenesis factor, and the c-Met signals in endothelial cells can induce many of the cellular responses required by angiogenesis (proliferation, mobility, penetration).

It is known that c-Met signal pathway plays an important role in the aspects of transformation, proliferation, survival, infiltration, and metastasis of cells. C-Met signal transduction pathway is closely related to tumorigenesis. It is shown that c-Met and the ligand HGF are overexpressed in many types of human cancers, and participated in oncogenesis. High levels of HGF and/or c-Met are observed in tumors of liver, breast, pancreas, lung, kidney, bladder, ovary, brain, prostate and gall bladder, myeloma as well as many other tumors. Many studies have found that the expression of c-Met and/or HGF are correlated to the state of progression of the above mentioned different kinds of cancers (Fabiola et al, European Journal of Cancer, 2010, 46:12601270).

Therefore, it can be seen that c-Met tyrosine kinase and the downstream regulated signal pathways thereof are important to the proliferation, differentiation and metastasis processes of tumor cells. Accordingly, the blockade of these signal pathways is considered to be an active means for treating cancers.

In summary, c-Met is considered to be an efficacious target for treating cancers. Inhibition on the activity of c-Met can effectively control the growth and metastasis of tumor cells, and enhance the sensitivity of tumor towards chemotherapy and radiotherapy. The research and development of inhibitors of c-Met have become a hot spot in studies of antitumor field.

WO 2009/099982 A1 discloses 2-aminopyridine compound having the following structure:

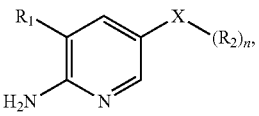

and regards that these compounds are inhibitors of tyrosine kinase (KDR, Tie-2, Flt3, FGFR3, Ab1, AuroraA, c-Src, IGF-IR, ALK, c-Met, RON, PAK1, PAK2, TAK1, etc.) that can be used to treat diseases mediated by protein kinase activities, and further discloses the following structure:

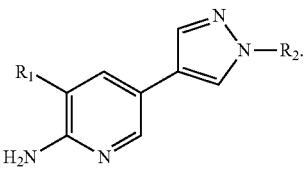

WO 2008/008539 A2 discloses a series of fused heterocyclic derivates having the following structure:

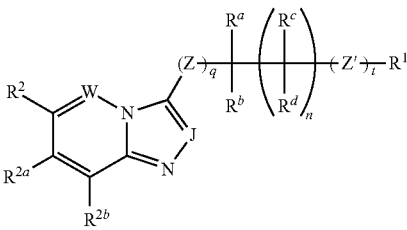

and regards that these compounds are inhibitors of c-Met.

WO 2008/071451 A1 discloses dihydropyridine derivatives having the following structure:

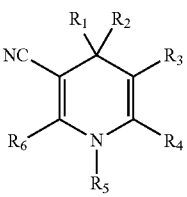

and indicates that these compounds have inhibitory activities on protein tyrosine kinase and can be used to treat c-Met mediated diseases.

US 2007/0265272 A1 discloses a compound having the following structure:

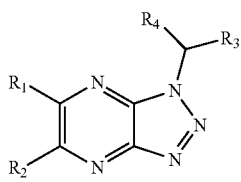

which is used to treat or prevent c-Met related diseases in mammals and treat proliferative diseases.

Among the therapeutic methods using c-Met as the target, some c-Met micromolecular kinase inhibitors have already entered the stage of clinical tests (Expert Opin. Ther. Patents, 2010, 20 (2): 159-177).

In summary, c-Met is the therapeutic target for tumor therapy with a promising development perspective. The efficient search of specific c-Met inhibitors with high potency and low toxicity has important clinical sense and application perspective, and has already become a hot spot in the current antitumor researches.

SUMMARY OF THE INVENTION

The present invention provides a compound of formula (I) and a pharmaceutically acceptable salt thereof:

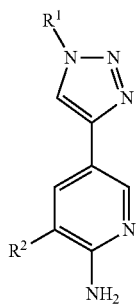

(I)

wherein:

$R^1$ is selected from H, $C_1$~$C_6$alkyl, $C_1$~$C_6$alkyl substituted by 1~3 halogen, $C_3$~$C_8$cycloalkyl, $C_3$~$C_8$cycloalkyl substituted by 1~3 halogen, —CONR'R", aryl, heteroaryl or nitrogen-containing saturated heterocyclyl;

$R^2$ is selected from —$OR^3$, —$SR^3$ or —$NR^3$, wherein $R^3$ is H, $C_1$~$C_6$alkyl, $C_1$~$C_6$alkyl substituted by 1~3 halogen, —(CR'R")$_{0~6}$-aryl, —(CR'R")$_{0~6}$-heteroaryl or —(CR'R")$_{0~6}$— nitrogen-containing saturated heterocyclyl; and wherein:

said aryl, heteroaryl and nitrogen-containing saturated heterocyclyl are unsubstituted or are substituted by halogen, $C_1$~$C_6$alkyl, $C_1$~$C_6$alkyl substituted by aryl, $C_1$~$C_6$alkoxy, $C_3$~$C_8$cycloalkyl, —NR'R", —COR''', —COOR''', —SOOR''' or —OH;

said R' and R" is each independently H, $C_1$~$C_4$alkyl or $C_1$~$C_4$alkyl substituted by 1~3 halogen; and said R''' is selected from the following groups: H, $C_1$~$C_4$alkyl, $C_1$~$C_4$alkyl substituted by 1~3 halogen, aryl that is unsubstituted or substituted by halogen, $C_1$~$C_4$alkyl, $C_1$~$C_4$alkoxy, —CN, —$NH_2$ or —OH, and heteroaryl that is unsubstituted or substituted by -halogen, $C_1$~$C_4$alkyl, $C_1$~$C_4$alkoxy, —CN, —$NH_2$ or —OH.

The present invention also provides a pharmaceutical composition containing said compound of formula (I) or a pharmaceutically acceptable salt thereof.

The present invention also provides said compound of formula (I) or a pharmaceutically acceptable salt thereof and a pharmaceutical composition containing said compound of formula (I) or a pharmaceutically acceptable salt thereof as a medicament for prevention and/or treatment of tumor.

The present invention also provides use of said compound of formula (I) or a pharmaceutically acceptable salt thereof and a pharmaceutical composition containing said compound of formula (I) or a pharmaceutically acceptable salt thereof in the preparation of a medicament for prevention and/or treatment of tumor.

The present invention also provides a method for prevention and/or treatment of tumor, comprising the step of administering to a subject in need thereof an effective amount of said compound of formula (I) or a pharmaceutically acceptable salt thereof or a pharmaceutical composition containing said compound of formula (I) or a pharmaceutically acceptable salt thereof.

The present invention also provides a method for preparing said compound of formula (I), said method comprises the following steps:

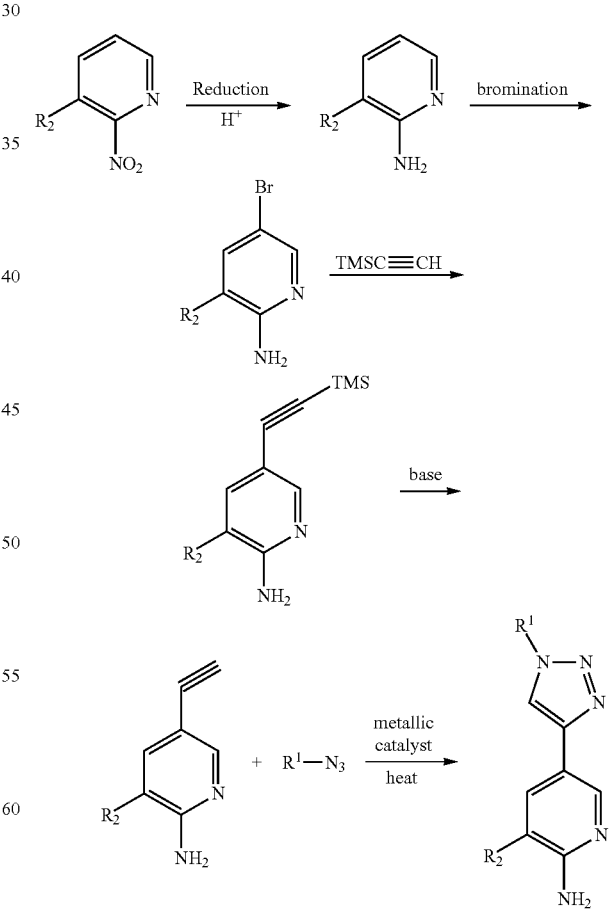

wherein $R^1$ and $R^2$ have the same meaning as those in the above formula (I).

In the present invention, term "aryl" means a aromatic cyclohydrocarbyl, preferably having 6~14 carbon atoms, more preferably an aryl having 6~10 carbon atoms, such as phenyl and naphthyl, more preferably phenyl.

In the present invention, term "heteroaryl" means a 5~6 membered monocyclic heteroaryl containing 1~4 heteroatoms selected from N, S and O or a bicyclic heteroaryl formed by fusing the aforesaid monocyclic heteroaryl and a benzene ring. Here, monocyclic heteroaryl is preferably furyl, thienyl, pyrrolyl, imidazolyl, pyrazolyl, thiazolyl, isothiazolyl, oxazolyl, isoxazolyl, triazolyl, tetrazolyl, thiadiazolyl, pyridyl, pyrimidinyl, pyridazinyl and pyrazinyl, especially preferably imidazolyl, thiazolyl, triazolyl, pyridiyl and pyrazinyl; bicyclic heteroaryl is preferably benzofuryl, benzothienyl, benzothiadiazolyl, benzothiazolyl, benzoimidazolyl, indolyl, isoindolyl, indazolyl, quinolinyl, isoquinolinyl and quinazolinyl.

In the present invention, term "nitrogen-containing saturated heterocyclyl" means a 4~6 membered saturated nitrogen-containing heterocyclyl containing at least one N atom and optional heteroatom(s) selected from O and S, preferably azetidinyl, pyrrolidinyl, pyrazolidinyl, imidazolidinyl, piperidyl, piperazinyl and morpholinyl, more preferably piperidyl, pyrrolidinyl, azetidinyl and morpholinyl.

In the present invention, term "halogen" means fluoro, chloro, bromo or iodo, preferably chloro and fluoro.

In the present invention, term "$C_1$~$C_6$alkyl" means an alkyl having 1 to 6 carbon atoms, including, but not limited to, such as methyl, ethyl, propyl, isopropyl, butyl, isobutyl, sec-butyl, tert-butyl, pentyl, hexyl and so on; preferably methyl, ethyl, propyl, isopropyl and butyl; term "$C_1$~$C_4$alkyl" means alkyl having 1 to 4 carbon atoms, including methyl, ethyl, propyl, isopropyl, butyl, isobutyl, sec-butyl and tert-butyl.

In the present invention, term "$C_1$~$C_6$alkoxy" means an alkoxy having 1 to 6 carbon atoms, including, but not limited to, such as methoxy, ethoxy, propoxy, isopropoxy, butoxy, isobutoxy, sec-butoxy, tert-butoxy, pentyloxy, hexyloxy and so on; preferably methoxy, ethoxy, propoxy, isopropoxy and butoxy; more preferably methoxy and ethoxy; term "$C_1$~$C_4$alkoxy" means alkoxy having 1 to 4 carbon atoms, including methoxy, ethoxy, propoxy, isopropoxy, butoxy, isobutoxy, sec-butoxy and tert-butoxy.

In the present invention, term "$C_3$~$C_8$cycloalkyl" means a saturated carboncyclic hydrocarbyl having 3 to 8 carbon atoms, including cyclopropyl, cyclobutyl, cyclopentyl, cyclohexyl, cycloheptyl and cyclooctyl; preferably cyclopropyl, cyclobutyl and cyclohexyl.

In the present invention, term "c-Met mediated diseases" means preliferative diseases resulted from the overexpression of c-Met/HGF such as tumors, especially malignant tumors, such as breast cancer, non small-cell lung cancer, ovarian cancer, gastric cancer, colon cancer, pancreatic cancer, epidermoid squamous carcinoma and so on.

In a preferable embodiment of the compound of formula (I) of the present invention, $R^2$ is selected from —$OR^3$ or —$SR^3$, especially —$OR^3$.

In a preferable embodiment, the compound of formula (I) of the present invention has the following structure of formula (II):

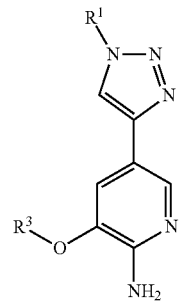

(II)

$R^1$ and $R^3$ in the formula have the same meaning as those in the above formula (I).

In a preferable embodiment of the compound of formula (II) of the present invention, $R^3$ is —(CR'R")$_{0-4}$-aryl or —(CR'R")$_{0-4}$-heteroaryl, said aryl or heteroaryl is unsubstituted or substituted by halogen, $C_1$~$C_4$alkyl or $C_1$~$C_4$alkoxy, said R' and R" are each independently H, $C_1$~$C_4$alkyl or $C_1$~$C_4$alkyl substituted by 1~3 halogen; in a more preferable embodiment, $R^3$ is —(CR'R")$_{1-2}$-aryl, said aryl is unsubstituted or substituted by halogen or $C_1$~$C_4$alkyl, said R' and R" are each independently H or —$C_1$~$C_4$alkyl; in a more preferable embodiment, $R^3$ is —(CR'R")—phenyl, said phenyl is substituted by halogen, said R' and R" are each independently H or methyl.

In a preferable embodiment of the compound of formula (II) of the present invention, $R^1$ is aryl, heteroaryl or nitrogen-containing saturated heterocyclyl, wherein said aryl, heteroaryl or nitrogen-containing saturated heterocyclyl is unsubstituted or substituted by halogen, $C_1$~$C_6$alkyl, $C_1$~$C_4$alkyl substituted by aryl, $C_1$~$C_6$alkoxy, $C_3$~$C_8$cycloalkyl, —$NH_2$, —COR''', —COOR''', —SOOR''' or —OH; said R''' is H, $C_1$~$C_4$alkyl substituted by 1~3 halogen, aryl that is unsubstituted or substituted by halogen, $C_1$~$C_4$alkyl, $C_1$~$C_4$alkoxy, —$NH_2$ or —OH, or heteroaryl that is unsubstituted or substituted by halogen, $C_1$~$C_4$alkyl, $C_1$~$C_4$alkoxy, —CN, —$NH_2$ or —OH.

In a more preferable embodiment of the compound of formula (II) of the present invention, $R^1$ is nitrogen-containing saturated heterocyclyl, said nitrogen-containing saturated heterocyclyl is unsubstituted or substituted by halogen, $C_1$~$C_6$alkyl, $C_1$~$C_2$alkyl substituted by aryl, $C_1$~$C_6$alkoxy, —$NH_2$, —COR''', —COOR''', —SOOR''' or —OH; said R''' is H, $C_1$~$C_4$alkyl, $C_1$~$C_4$alkyl substituted by 1~3 halogen, aryl that is unsubstituted or substituted by halogen, $C_1$~$C_4$alkyl, $C_1$~$C_4$alkoxy, —CN, —$NH_2$ or —OH, or heteroaryl that is unsubstituted or substituted by halogen, $C_1$~$C_4$alkyl, $C_1$~$C_4$alkoxy, —CN, —$NH_2$ or —OH.

In a more preferable embodiment of the compound of formula (II) of the present invention, $R^1$ is nitrogen-containing saturated heterocyclyl, said nitrogen-containing saturated heterocyclyl is unsubstituted or substituted by halogen, $C_1$~$C_4$alkyl, $C_1$~$C_2$alkyl substituted by phenyl, $C_1$~$C_4$alkoxy, —$NH_2$, —COR''', —COOR''', —SOOR''' or —OH; said R''' is H, $C_1$~$C_4$alkyl, $C_1$~$C_4$alkyl substituted by 1~3 halogen, aryl that is unsubstituted or substituted by halogen, $C_1$~$C_4$alkyl, $C_1$~$C_4$alkoxy, —CN, —$NH_2$ or —OH, or heteroaryl that is unsubstituted or substituted by halogen, $C_1$~$C_4$alkyl, $C_1$~$C_4$alkoxy, —CN, —$NH_2$ or —OH.

In a more preferable embodiment of the compound of formula (II) of the present invention, $R^1$ is piperidyl, pyrrolidinyl, pyrazolidinyl, azetidinyl or morpholinyl, wherein said piperidyl, pyrrolidinyl, pyrazolidinyl, azetidinyl and morpholinyl is unsubstituted or substituted by halogen, $C_1 \sim C_4$alkyl, $C_1 \sim C_4$alkyl substituted by aryl, $C_1 \sim C_4$alkoxy, —COR''', —COOR''', —SOOR''', —NH$_2$ or —OH; said R''' is H, $C_1 \sim C_4$alkyl substituted by 1~3 halogen, aryl that is unsubstituted or substituted by halogen, $C_1 \sim C_4$alkyl, $C_1 \sim C_4$alkoxy, —CN, —NH$_2$ or —OH, or heteroaryl that is unsubstituted or substituted by halogen, $C_1 \sim C_4$alkyl, $C_1 \sim C_4$alkoxy, —CN, —NH$_2$ or —OH.

In a more preferable embodiment of the compound of formula (II) of the present invention, $R^1$ is piperidyl, said piperidyl is unsubstituted or substituted by $C_1 \sim C_4$alkyl, —COR''', —COOR''', —SOOR''' or $C_1 \sim C_2$alkyl substituted by phenyl; said R''' is H, $C_1 \sim C_4$alkyl substituted by 1~3 halogen, phenyl that is unsubstituted or substituted by halogen, $C_1 \sim C_4$alkyl, $C_1 \sim C_4$alkoxy, —CN, —NH$_2$ or —OH, thiazolyl that is unsubstituted or substituted by halogen, $C_1 \sim C_4$alkyl, $C_1 \sim C_4$alkoxy, —CN, —NH$_2$ or —OH, imidazolyl that is unsubstituted or substituted by halogen, $C_1 \sim C_4$alkyl, $C_1 \sim C_4$alkoxy, —CN, —NH$_2$ or —OH, pyridiyl that is unsubstituted or substituted by halogen, $C_1 \sim C_4$alkyl, $C_1 \sim C_4$alkoxy, —CN, —NH$_2$ or —OH, or pyrazinyl that is unsubstituted or substituted by halogen, $C_1 \sim C_4$alkyl, $C_1 \sim C_4$alkoxy, —CN, —NH$_2$ or —OH.

In a more preferable embodiment of the compound of general formula (II) of the present invention, $R^1$ is piperidyl that is unsubstituted or substituted by $C_1 \sim C_4$alkyl, $C_1 \sim C_2$alkyl substituted by phenyl, —COR''', —COOR''' or —SOOR''', said R''' is $C_1 \sim C_4$alkyl or phenyl substituted by halogen, $C_1 \sim C_4$alkyl or —CN.

In the present invention, the specifically preferable compound of general formula (I) includes the following compounds and pharmaceutically acceptable salts thereof:

3-(1-(2,6-dichloro-3-fluorophenyl)ethoxy)-5-(1-(1-tert-butyl formate-piperidin-4-yl)-1H-1,2,3-triazol-4-yl)-2-aminopyridine;
3-(1-(2,6-dichloro-3-fluorophenyl)ethoxy)-5-(1-(piperidin-4-yl)-1H-1,2,3-triazol-4-yl)-2-aminopyridine;
3-(1-(2,6-dichloro-3-fluorophenyl)ethoxy)-5-(1-(1-benzylpiperidin-4-yl)-1H-1,2,3-triazol-4-yl)-2-aminopyridine;
3-(1-(2,6-dichloro-3-fluorophenyl)ethoxy)-5-(1-(1-p-cyanobenzoylpiperidin-4-yl)-1H-1,2,3-triazol-4-yl)-2-aminopyridine;
3-(1-(2,6-dichloro-3-fluorophenyl)ethoxy)-5-(1-(1-p-fluorobenzoylpiperidin-4-yl)-1H-1,2,3-triazol-4-yl)-2-aminopyridine;
3-(1-(2,6-dichloro-3-fluorophenyl)ethoxy)-5-(1-(1-p-tosylpiperidin-4-yl)-1H-1,2,3-triazol-4-yl)-2-aminopyridine;
3-(1-(2,6-dichloro-3-fluorophenyl)ethoxy)-5-(1-(1-mesylpiperidin-4-yl)-1H-1,2,3-triazol-4-yl)-2-aminopyridine;
3-(1-(2,6-dichloro-3-fluorophenyl)ethoxy)-5-(1-(1-methylpiperidin-4-yl)-1H-1,2,3-triazol-4-yl)-2-aminopyridine;
3-(1-(2,6-dichloro-3-fluorophenyl)ethoxy)-5-(1-((1-diphenylmethyl) azetidin-3-yl)-1H-1,2,3-triazol-4-yl)-2-aminopyridine;
3-(1-(2,6-dichloro-3-fluorophenyl)ethoxy)-5-(1-(azetidin-3-yl)-1H-1,2,3-triazol-4-yl)-2-aminopyridine;
(S)—N-tert-butyloxycarbonyl-(4-(6-amino-5-(1-(2,6-dichloro-3-fluor ophenyl)ethoxy)pyridin-3-yl)-1H-1,2,3-triazol-1-yl)piperidine;
(S)-3-(1-(2,6-dichloro-3-fluorophenylethoxy)-5-(1-(piperidin-4-yl)-1H-1,2,3-triazol-4-yl)-2-aminopyridine; and
(R)-3-(1-(2,6-dichloro-3-fluorophenyl)ethoxy)-5-(1-(piperidin-4-yl)-1 H-1,2,3-triazol-4-yl)-2-aminopyridine In an embodiment of the preparation method of the compound of formula (I) of the present invention, said method includes the following steps:

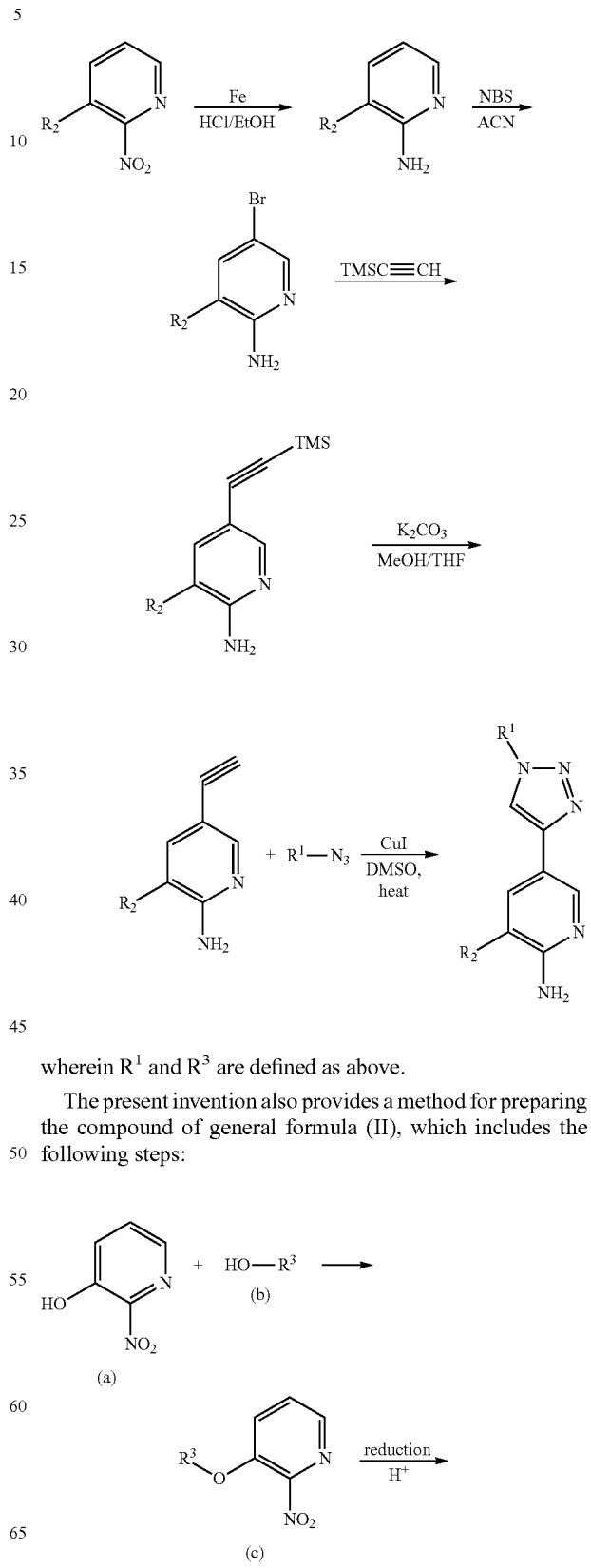

wherein $R^1$ and $R^3$ are defined as above.

The present invention also provides a method for preparing the compound of general formula (II), which includes the following steps:

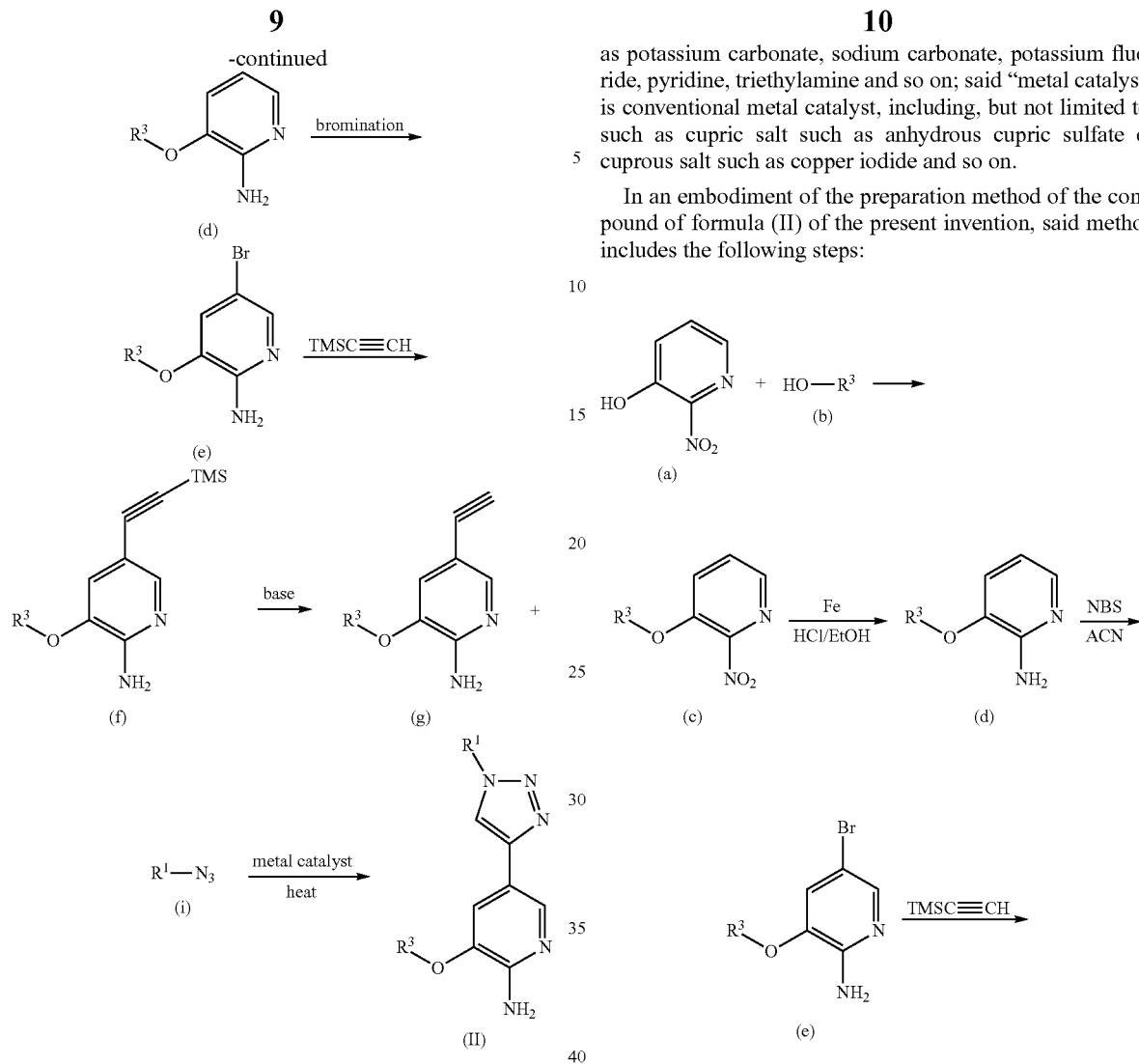

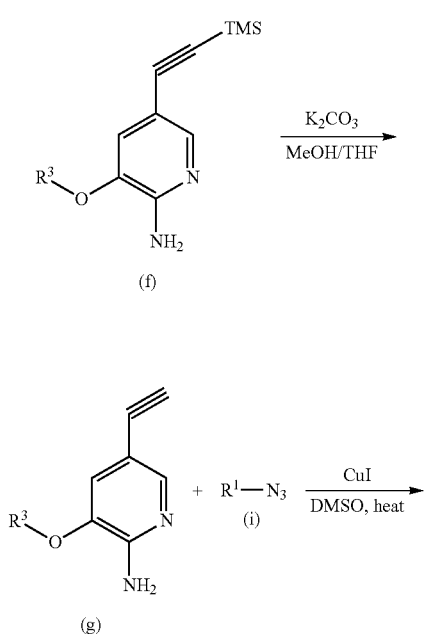

wherein $R^1$ and $R^3$ have the same meaning as those in the above formula (I);

3-hydroxy-2-nitropyridine, as the starting material, is reacted with compound (b) via nucleophilic substitution to yield compound (c); the compound (c) is converted to compound (e) via reduction, bromination; the compound (e) and trimethylsilylethyne are converted to compound (f) under the catalysis of a transition metal catalyst; the compound (f) is converted to compound (g) under the effect of a base; the compound (g) is reacted with organic azide (i) under the catalysis of a metal catalyst to yield the final product, i.e. the compound of general formula (II).

In the method for preparing the compounds of the present invention, said "reduction" is effected by conventional reductants well known in the art, including, but not limited to, such as iron powder, zinc dust, sodium sulfide and so on; said "bromination" is effected by conventional brominating agents well known in the art, including, but not limited to, such as N-bromosuccimide, bromine water, liquid bromine and so on; said "transition metal catalyst" is conventional transition metal catalyst customarily used in the art, including, but not limited to, such as bis(triphenylphosphine)palladium dichloride, tetrakis(triphenylphosphine) palladium, 1,1'-bis(diphenylphosphine)ferrocene palladium dichloride, palladium acetate and so on; said "base" is conventional inorganic or organic base, including, but not limited to, such as potassium carbonate, sodium carbonate, potassium fluoride, pyridine, triethylamine and so on; said "metal catalyst" is conventional metal catalyst, including, but not limited to, such as cupric salt such as anhydrous cupric sulfate or cuprous salt such as copper iodide and so on.

In an embodiment of the preparation method of the compound of formula (II) of the present invention, said method includes the following steps:

-continued

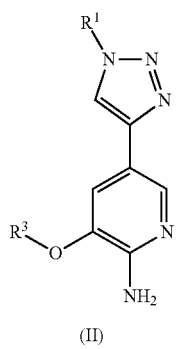

wherein R¹ and R³ have the same meaning as those in the above formula (I),

In the compound of formula (I) of the present invention, when R² is selected from —SR³ or —NR³, the starting material

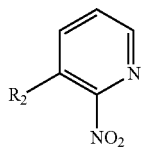

in the synthesis process can be prepared by the following method:

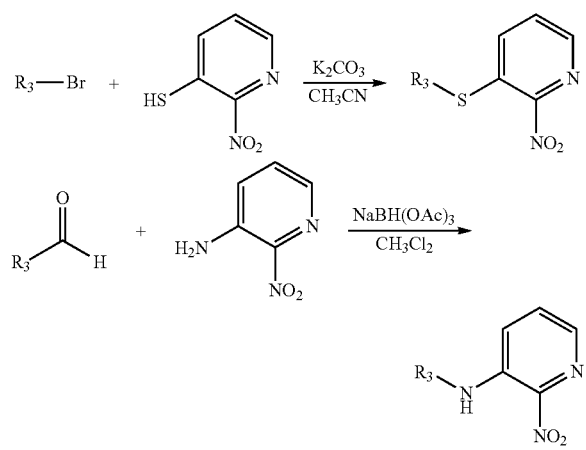

wherein R³ have the same meaning as those in the above formula (I).

In each of the above mentioned preparation steps, the abbreviations for the utilized agents are respectively denoted as:
ACN acrylonitrile
CH₃CN acetonitrile
CuI cuprous iodide
DMSO dimethyl sulfoxide
EtOH ethanol
HCl hydrochloric acid
K₂CO₃ potassium carbonate
MeOH methanol
NaBH(OAc)₃ sodium triacetoxyborohydride
NBS N-bromosuccimide
THF tetrahydrofuran
TMSC≡CH trimethylsilylethyne The present invention also includes the pharmaceutically acceptable salt of the compound of formula (I). The term "pharmaceutically acceptable salt" means relatively nontoxic acid addition salts or base addition salts of the compound of the present invention. Said acid addition salts are the salts formed between the compound of formula (I) of the present invention and suitable inorganic acids or organic acids, said salts may be prepared during the final separation and purification processes of the compounds, or may be prepared through the reaction of purified compound of formula (I) in the form of free base thereof and suitable organic acids or inorganic acids. Representative acid addition salts includes hydrobromic acid salt, hydrochloric acid salt, sulfate, sulfite, acetate, oxalate, valerate, oleate, palmate, stearate, laurate, borate, benzoate, lactate, phosphate, toylformate, citrate, maleate, fumarate, succinate, tartrate, benzoate, mesylate, p-tosylate, glyconate, lactobionate and laurylsulfonate and so on. Said base addition salts are the salts formed between the compound of formula (I) and suitable inorganic bases or organic bases, including such as the salts formed with alkali metals, alkaline earth metals, quaternary ammonium cations, such as sodium salts, lithium salts, potassium salts, calcium salts, magnesium salts, tetramethyl quaternary ammonium salts, tetraethyl quaternary ammonium salt and so on; including the salts formed with ammonia (NH₃), primary amines, secondary amines or tertiary amines, such as: methylamine salts, dimethylamine salts, trimethylamine salts, triethylamine salts, ethylamine salts and so on.

It has been experimentally demonstrated that the compounds of the present invention have c-Met inhibitory activity, and can be used to prevent and/or treat diseases that can be relieved or treated via the inhibition on c-Met, said diseases including tumors, especially malignant tumors, such as breast cancer, non small-cell lung cancer, ovarian cancer, gastric cancer, colon cancer, pancreatic cancer, epidermoid squamous carcinoma and so on.

Accordingly, the present invention also provides the use of the compound of formula (I) in the preparation of a medicament for the prevention and/or treatment of diseases that can be relieved or treated via the inhibition on c-Met, especially tumors.

The compound of formula (I) of the present invention or a pharmaceutically acceptable salt thereof can be administered to mammals, such as human. The doses may be administered orally, rectally, parenterally (intravenously, intramuscularly or subcutaneously), and topically (such as in the form of powder, ointment or drops and so on).

Accordingly, the present invention also provides a pharmaceutical composition containing the compound of formula (I) of the present invention or a pharmaceutically acceptable salt thereof as active ingredients, and pharmaceutically acceptable carriers, excipients or diluents. When preparing the pharmaceutical composition, the compound of formula (I) of the present invention or a pharmaceutically acceptable salt thereof is generally admixed with pharmaceutically acceptable carriers, excipients or diluents.

Through conventional preparation methods, the composition of the present invention may be formulated into conventional pharmaceutical preparations, such as tablets, pills, capsules, powder, granules, emulsions, suspensions, dispersions, solutions, syrups, elixirs, ointment, drops, suppositories, inhalants, propellants and so on.

The solid dosage forms for oral administration of the composition of present invention includes such as capsules, tablets, pills, powder and granules and so on. In these solid dosage forms, the compounds of formula (I) of the present invention as active ingredients are admixed with at least one conventional inert excipients (or carriers), such as sodium citrate or dicalcium phosphate, or admixed with the following ingredients: (a) filling materials or extenders, such as, starch, lactose, sucrose, glucose, mannitol and silicic acid and so on; (b) adhesives, such as, hydroxymethylcellulose, alginate, gelatin, polyvinyl pyrrolidine, sucrose and acacia and so on; (c) humectants, such as, glycerol and so on; (d) disintegrating agents, such as, agar, calcium carbonate, potato starch or tapioca, alginic acid, certain composite silicate and sodium carbonate and so on; (e) retarding solvents, such as paraffin wax and so on; (f) absorption accelerators, such as, quaternary ammonium compounds and so on; (g) moistening agents, such as cetanol and glyceryl monostearate and so on; (h) absorbents, such as, kaolin and so on; and (i) lubricants, such as, talc, calcium stearate, magnesium stearate, solid polyethylene glycol, sodium dodecyl sulphate and so on, or mixtures thereof. Capsules, tablets and pills may also comprise buffers.

Said solid dosage forms such as tablets, sugar pills, capsules, pills and granules can also by coated or microencapsulated by coatings and shell materials such as enteric coatings and other materials well known in the art. They may comprise opacifying agents, and the release of active ingredients in these compositions may be occurred in a certain portion of digestive tube in a retarded manner. The examples for embedding components that may be adopted are polymers and waxes. If necessary, active ingredients may also formulated into the form of microcapsules with one or more of the above excipients.

The liquid dosage forms for oral administration of the composition of present invention includes pharmaceutically acceptable emulsions, solutions, suspensions, syrups and tinctures and so on. Besides the compounds of formula (I) as active ingredients, the liquid dosage forms may comprise inert diluents customarily used in the art, such as water or other solvents, solubilizers and emulsifiers, such as, ethanol, isopropyl alcohol, ethyl carbonate, ethyl acetate, propylene glycol, 1,3-butanediol, dimethyl formamide and oils, especially cottonseed oil, peanut oil, corn germ oil, olive oil, castor oil and sesame oil and so on or mixtures of these materials and so on.

Besides these inert diluents, the liquid dosage forms of the present invention may also comprise conventional accessory ingredients, such as moistening agents, emulsifiers and suspending agents, sweeting agents, flavoring agents and aromatic spices and so on.

Said suspending agents includes, such as, ethoxylated isostearyl alcohol, polyoxyethylene sorbitol and sorbitan ester, microcrystalline cellulose, aluminium methoxide and agar and so on or mixtures of these materials.

The dosage forms for parenteral injection of the composition of present invention may include physiologically acceptable sterile aqueous or anhydrous solutions, dispersions, suspensions or emulsions, and sterile powder for re-dissolving into sterile injectable solutions or dispersions. Suitable carriers, diluents, solvents or excipients include water, ethanol, polyhydric alcohol and suitable mixtures thereof.

The dosage form of the preparation of the compound of the present invention for topical administration includes ointments, powder, suppositories, drops, propellants and inhalants and so on. The compounds of formula (I) of the present invention as active ingredients are admixed together with physiologically acceptable carriers and optional preservatives, buffers, or propellants that may be required when necessary, under sterile condition.

Accordingly, the present invention also provides a pharmaceutical preparation containing 0.1~500 mg of the compounds of formula (I) of the present invention or a pharmaceutically acceptable salt thereof, and pharmaceutically acceptable carriers, excipients or diluents.

The present invention also provides a method for treating tumors that can be relieved or treated via the inhibition on the activity of c-Met, including the step of administering to a patient in need of treatment 0.1~50 mg/kg body weight/day of the compound of formula (I) of the present invention or a pharmaceutically acceptable salt thereof.

It has been demonstrated through cell experiments and animal experiments that the compound of formula (I) of the present invention has inhibitory effect on the proliferation of cancer cells and inhibitory effect on the growth of transplanted tumors and can be used to treat cancer and prepare a medicament for treating cancer.

The pharmacodynamic action of the compound of the present invention in terms of inhibiting the proliferation of cancer cells may be assayed by conventional methods, one preferable evaluation method of which is Sulforhodamine B (SRB) protein staining method, which calculates the inhibition ratio of a drug against the proliferation of cancer cells through measuring the change in optical absorption value generated after the drug has influenced the cancer cells.

Inhibition ratio (%)=(OD control−OD inhibitor−OD blank)/(OD control−OD blank)×100%

OD control: the OD value of the well of normally grown cells without the action of a drug.

OD inhibitor: the OD value of the well of cells with the action of added compounds to be screened.

OD blank: the OD value of the well of parallel control without seeding cells.

The median inhibitory concentration ($IC_{50}$) value is obtained by the software GraphPad Prism 5 through calculation.

The pharmacodynamic action of the compound of the present invention in terms of inhibiting the growth of transplanted tumors in animal may be assayed by conventional methods, one preferable evaluation method of which is the inhibitory effect on the growth of subcutaneously transplanted tumors of human lung cancer H1975 in nude mice. The experimental method is as follows: human lung cancer H1975 cell strain ($5\times10^6$/each mouse) was inoculated to nude mice subcutaneously at the side of the body thereof. The diameter of subcutaneous transplanted tumors of nude mice was measured by a vernier caliper. After the tumors had grown to 100 mm$^3$, the animals were divided into groups randomly. The test compounds were administered by intragastric administration in different dosages, and solvent control groups were administered with equal amount of solvent by intragastric administration, wherein the administration was performed once daily for a continuous 14 days. During the entire experimental process, the diameter of transplanted tumors was measured every two weeks, and the body weight of the mice was measured simultaneously so as to observe if toxic reactions were occurred. The computational formula of tumor volume (Tumor, TV) is:

TV=½×a×b$^2$, wherein a and b denote length and width respectively.

Through the Western blot test, it was also demonstrated that the compound of the present invention has the c-Met inhibitory activity, can effectively inhibit the phosphorylation of c-Met, has the c-Met inhibitory activity.

The evaluation of the inhibition of the compound of the present invention on the activity of c-Met enzyme in molecular level may be assayed by conventional methods, one preferable evaluation method of which is enzyme-linked immunosorbent assay (ELISA). By measuring the inhibition ratio of the compounds against the activity of receptor tyrosine kinase protein c-Met enzyme, the median inhibitory concentration $IC_{50}$ is calculated based on the inhibition ratios for various concentrations using the four-parameter method.

The inhibition ratio for a sample (%)=(1−(OD value of a compound−OD value of the control well without enzyme)/(OD value of the negative control well−OD value of the control well without enzyme))×100%

Figure 1:
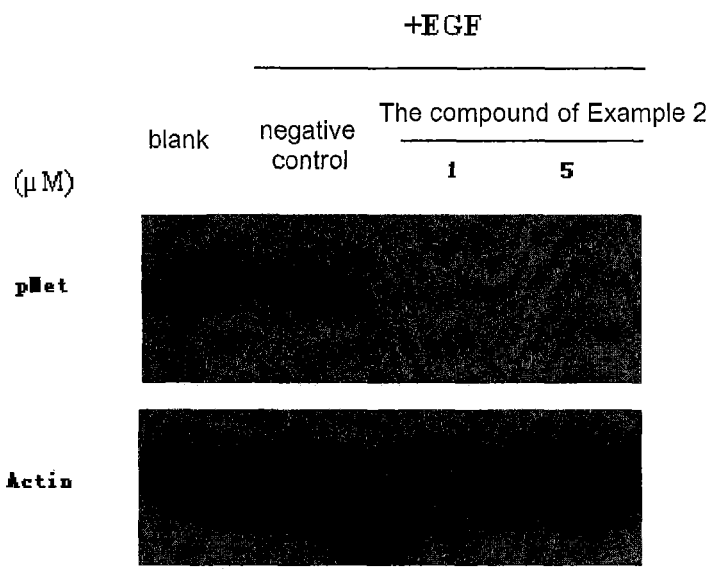
FIG. 1 is the Western blot test figure of the inhibition of the compound of Example 2 against the phosphorylation of c-Met.

The present invention will be further illustrated hereinafter in connection with specific Examples. It should be understood that these Examples are only used to illustrate the present invention without limiting the scope thereof. In the following Examples, the experimental methods without specifying conditions are generally performed according to conventional conditions or based on the conditions recommended by the manufacturer. The parts and percentages are parts by weight and weight percentage respectively, unless otherwise specified.

SPECIFIC MODE FOR CARRYING OUT THE INVENTION

I. Preparation Examples for the Compounds of the Present Invention

Example 1

The synthesis of 3-(1-(2,6-dichloro-3-fluorophenyl)ethoxy)-5-(1-(1-tert-butyl formatepiperidin-4-yl)-1H-1,2,3-triazol-4-yl)-2-aminopyridine (Compound 1)

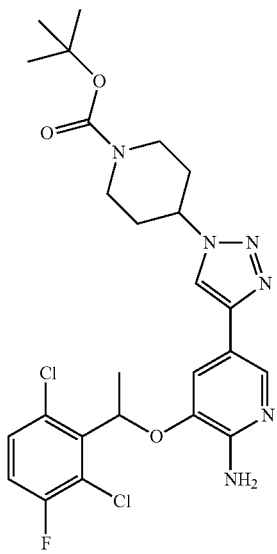

The title compound was prepared by the following steps.

1) The synthesis of 1-(2,6-dichloro-3-fluorophenyl)ethanol

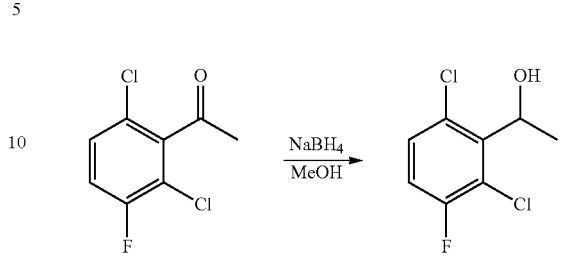

2,6-dichloro-3-fluorophenylethylketone (40.0 g, 0.19 mol) was dissolved in anhydrous methanol (300 mL), and NaBH$_4$ (17.5 g, 0.24 mol) was added portionwise under ice bath. After 1 h, the pH was adjusted to pH=1 using 2N HCl. Methanol solvent was evaporated under reduced pressure. To the residue were added dichloromethane (300 mL) and water (300 mL), and the organic phase was separated, washed with saturated brine, dried over anhydrous sodium sulfate and then sucking filtered. The filtrate was evaporated under reduced pressure to remove dichloromethane, and then purified via silica gel column chromatography (petroleum ether:ethyl acetate=30:1) to yield the target product as light yellow liquid (39.8 g, 0.186 mol; yield=98%).

$^1$H-NMR (CDCl$_3$, 400 MHz): δ ppm 1.64 (d, J=6.82 Hz, 3H), 3.02 (d, J=9.85 Hz, 1H), 6.97-7.07 (m, 1H), 7.19-7.33 (m, 1H).

ESI (+) m/z: 209

2) The synthesis of 3-(1-(2,6-dichloro-3-fluorophenyl)ethoxy)-2-nitropyridine

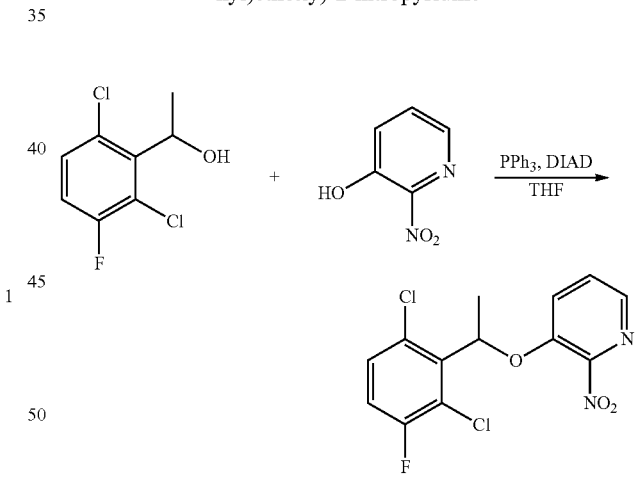

1-(2,6-dichloro-3-fluorophenyl)ethanol (29.1 g, 139 mmol) and 3-hydroxy-2-nitropyridine (24.1 g, 153 mmol) were dissolved in anhydrous tetrahydrofuran (300 mL), and triphenylphosphine (PPh$_3$, 51.1 g, 195 mmol) was added and the mixture was stirred for 1 h at room temperature. At 0° C., to the reaction liquid was added diisopropyl azodicarboxylate (DIAD, 38.4 mL, 195 mmol) dropwise. The resultant mixture was stirred overnight at room temperature. The resultant mixture was evaporated under reduced pressure to remove solvent, then purified via silica gel column chromatography (petroleum ether:ethyl acetate=3:1) to yield the target product as white crystals (41.2 g, 124 mmol; yield=89%).

$^1$H-NMR (CDCl$_3$, 400 MHz): δ ppm 1.80-1.85 (d, 3H), 6.00-6.15 (q, 1H), 7.0-7.1 (t, 1H), 7.2-7.21 (d, 1H), 7.25-7.5 (m, 2H), 8.0-8.05 (d, 1H).

ESI (+) m/z: 331

3) The synthesis of 3-(1-(2,6-dichloro-3-fluorophenyl)ethoxy)-2-aminopyridine

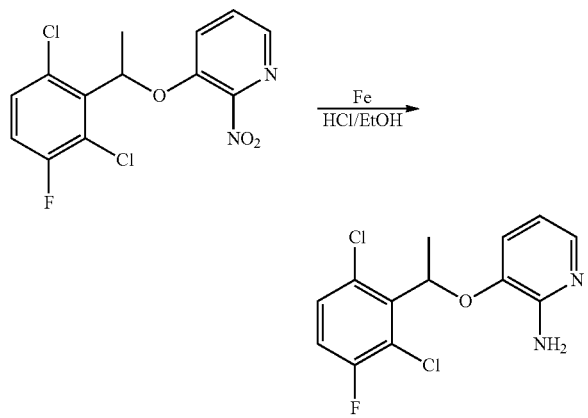

3-(1-(2,6-dichloro-3-fluorophenyl)ethoxy)-2-nitropyridine (56.7 g, 171 mmol) was dissolved in ethanol (354 mL), 2N HCl (35.4 mL) was added, and iron powder (67.0 g, 1196 mmol) was added portionwise under the cooling of ice bath. After 15 min, it was warmed to 85° C. After 1 h, the reaction liquid was cooled to room temperature, to which was added diatomaceous earth (85 g). After stirring for 15 min, the reaction liquid was sucking filtered using diatomaceous earth. The filtrate was evaporated to dryness under reduced pressure to yield the target product as light yellow solid powder (48.2 g, 160 mmol; yield=94%).

$^1$H-NMR (CDCl$_3$, 400 MHz): δ ppm 1.80-1.85 (d, 3H), 4.9-5.2 (brs, 2H), 6.7-6.84 (q, 1H), 7.0-7.1 (m, 1H), 7.2-7.3 (m, 1H), 7.6-7.7 (m, 1H).

4) The synthesis of 5-bromo-3-(1-(2,6-dichloro-3-fluorophenyl)ethoxy)-2-aminopyridine

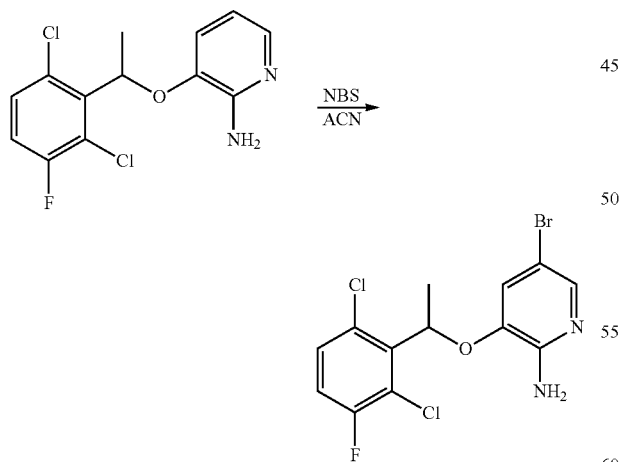

3-(1-(2,6-dichloro-3-fluorophenyl)ethoxy)-2-aminopyridine (24.0 g, 79.9 mmol) was dissolved in acetonitrile (250 mL), and to which was added NBS (14.2 g, 79.9 mmol) under the cooling of ice bath. After 15 min, the solvent in the resultant mixture was evaporated under reduced pressure, and then purified via silica gel column chromatography (petroleum ether:ethyl acetate=3:1) to yield the target product as solid powder of soil colour (23.2 g, 61.1 mmol; yield=76%).

$^1$H-NMR (CDCl$_3$, 400 MHz): δ ppm 1.85-1.95 (d, 3H), 4.7-5.0 (brs, 2H), 5.9-6.0 (q, 1H), 6.8-6.95 (d, 1H), 7.01-7.2 (t, 1H), 7.4-7.45 (m, 1H), 7.8-7.85 (d, 1H).

5) The synthesis of N-tert-butyloxycarbonyl-4-piperidinemethanesulfonate

N-tert-butyloxycarbonyl-4-piperidinol (50.0 g, 249 mmol) was dissolved in dry dichloromethane (300 mL). And triethylamine (TEA, 34.9 mL, 249 mL), methylsulfonyl chloride (MsCl, 19.3 mL, 249 mL) and DMAP (4-dimethylaminopyridine) (302 mg, 2.5 mmol) was slowly added successively under the cooling of ice bath. The temperature was raised to room temperature, and the reaction was performed overnight. To the resultant mixture was added water (200 mL), the organic phase was separated, washed with water and saturated brine successively, dried over anhydrous sodium sulfate. After sucking filtration, the filtrate was evaporated to dryness under reduced pressure to yield the target product as white solid powder (69.5 g, 249 mmol; yield=100%).

6) The synthesis of N-tert-butyloxycarbonyl-4-azidopiperidine

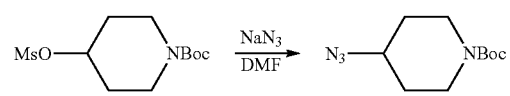

N-tert-butyloxycarbonyl-4-piperidinemethanesulfonate (10.0 g, 36 mmol) was dissolved in DMF (100 mL), sodium azide (NaN$_3$, 7.0 g, 108 mmol) was added, the reaction mixture was warmed to 100° C., and the reaction was performed overnight. The solvent in the resultant mixture was evaporated under reduced pressure, water (100 mL) and ethyl acetate (100 mL) were added, the organic phase was separated, washed with water (100 mL×2) and saturated brine successively, dried over anhydrous sodium sulfate, and then evaporated under reduced pressure to remove ethyl acetate so as to yield the target product as light yellow liquid (8.2 g, 36 mmol; yield=100%). The crude produce was directly used for the reaction in the next step.

7) The synthesis of 5-trimethylsilylethynyl-3-(1-(2,6-dichloro-3-fluorophenyl)ethoxy)-2-aminopyridine

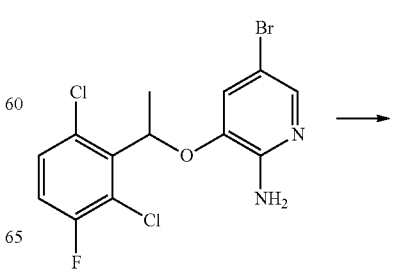

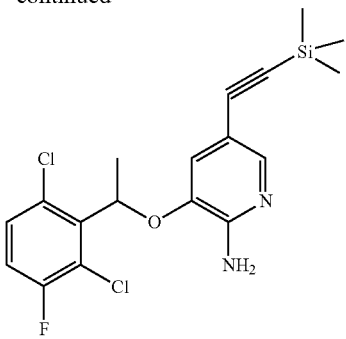

5-bromo-3-(2,6-dichloro-3-fluoro-benzyloxy)-pyridine-2-amine (3.8 g, 10 mmol), trimethylsilylethyne (3.87 mL, 28 mmol), triethylamine (Et₃N, 4.15 mL, 30 mmol), triphenylphosphine (PPh₃, 52 mg, 0.2 mmol) and bis(triphenylphosphine)palladium dichloride (PdCl₂(PPh₃)₂, 140.3 mg, 0.2 mmol) was dissolved in N,N-dimethyl formamide (DMF, 10 mL), to which argon gas was bubbled for 10 min, then CuI (19 mg, 0.1 mmol) was added, the resultant reaction liquid was stirred under heating at 90° C. After 4.5 h, the reaction liquid was cooled to room temperature, water (10 mL) was added to quench the reaction. The resultant mixture was extracted with ethyl acetate (3×20 mL), the organic phases were combined, washed with water and saturated brine successively, dried over anhydrous sodium sulfate, and then concentrated, the resultant residue was purified via silica gel column chromatography (PE/EA=3:1) to yield 2.5 g of the target product as brown solid.

¹H-NMR (CDCl₃, 400 MHz): δ 7.77 (d, 1H), 7.29 (m, 1H), 7.07 (q, 1H), 6.012 (d, 1H), 5.00 (br, 2H), 1.81 (d, 3H), 1.6 (s, 9H).

8) The synthesis of 5-ethynyl-3-(1-(2,6-dichloro-3-fluorophenyl)ethoxy)-2-aminopyridine

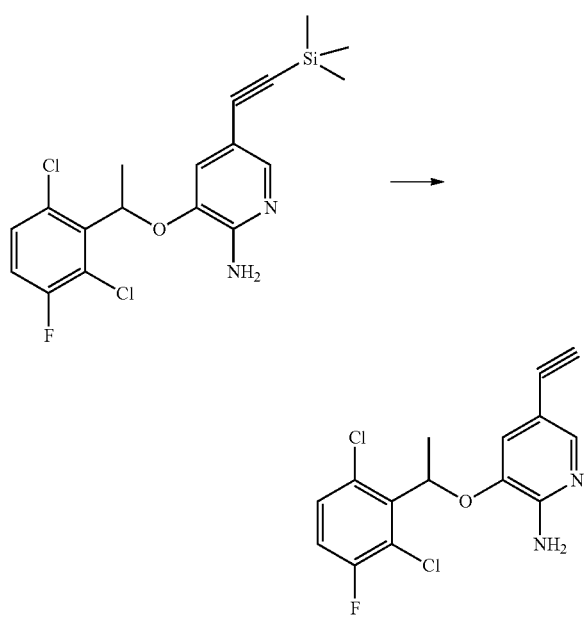

5-trimethylsilylethynyl-3-(1-(2,6-dichloro-3-fluorophenyl)ethoxy)-2-aminopyridine (1.5 g, 3.77 mmol) was dissolved in the mixed solvent of THF (10 mL) and MeOH (10 mL), K₂CO₃ (1.04 g, 7.55 mmol) was added, and the mixture was stirred for 2 h at room temperature. The majority of the solvent was removed under reduced pressure, water (10 mL) was added. The resultant mixture was extracted with ethyl acetate (3×20 mL), the organic phases were combined, washed with water and saturated brine successively, dried over anhydrous sodium sulfate, and then concentrated, the resultant residue was purified via silica gel column chromatography (petroleum ether/ethyl acetate=3:1) to yield 850 mg of the target product as brown solid.

¹H-NMR (CDCl₃, 400 MHz): δ 7.78 (d, 1H), 7.29-7.35 (m, 1H), 7.08-7.13 (t, 1H), 6.04 (d, 1H), 5.17 (br, 2H), 3.02 (s, 1H), 1.81 (d, 3H).

9) The synthesis of 3-(1-(2,6-dichloro-3-fluorophenyl)ethoxy)-5-(1-(1-tert-butyl formatepiperidin-4-yl)-1H-1,2,3-triazol-4-yl)-2-aminopyridine

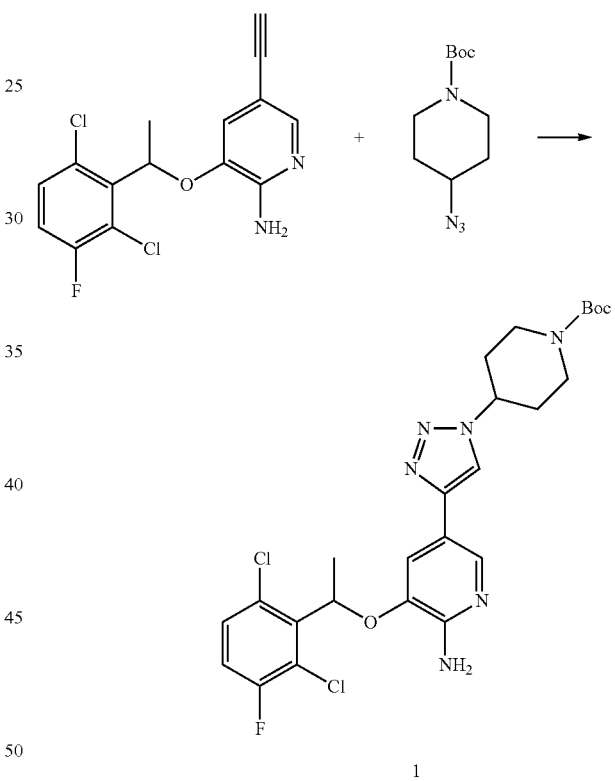

5-ethynyl-3-(1-(2,6-dichloro-3-fluorophenyl)ethoxy)-2-aminopyridine (3.25 g, 10 mmol) and N-Boc-4-azido-piperidine (3.39 g, 15 mmol) were dissolved in MeOH (20 mL), N,N-diisopropylethylamine (DIPEA, 6.43 g, 50 mmol) and CuI (57 mg, 3 mmol) were added successively. The reaction liquid was stirred overnight at room temperature, then filtered. The filtrate was concentrated, to the residue were added ethyl acetate (30 mL) and HCl (0.1M, 20 mL), the organic phase was separated, the water phase was extracted with ethyl acetate (3×20 mL), the organic phases were combined, washed with water and saturated brine successively, dried over anhydrous sodium sulfate, and then concentrated. The residue was recrystallized with MeOH to yield 3.2 g of the target product as light yellow solid.

¹H-NMR (CDCl₃, 400 MHz): δ 7.6 (s, 1H), 7.39 (s, 1H), 7.26-7.32 (m, 1H), 7.02-7.06 (t, 1H), 6.16 (d, 1H), 5.17 (br, 2H), 4.60-4.62 (m, 1H), 4.25-4.29 (m, 2H), 2.93-2.98 (m, 2H), 2.21-2.25 (m, 2H), 1.96-2.02 (m, 2H), 1.87 (d, 3H), 1.5 (s, 9H).

ESI (+) m/z: 551

Example 2

The synthesis of 3-(1-(2,6-dichloro-3-fluorophenyl)ethoxy)-5-(1-(piperidin-4-yl)-1H-1,2,3-triazol-4-yl)-2-aminopyridine (Compound 2)

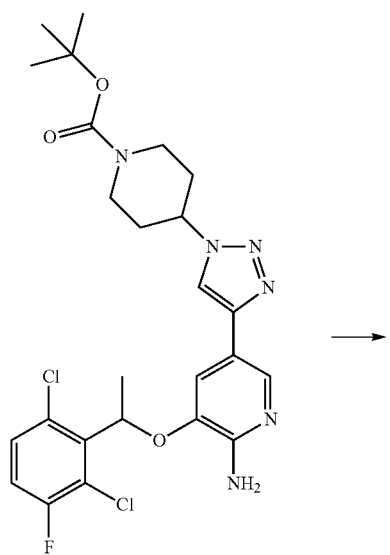

1

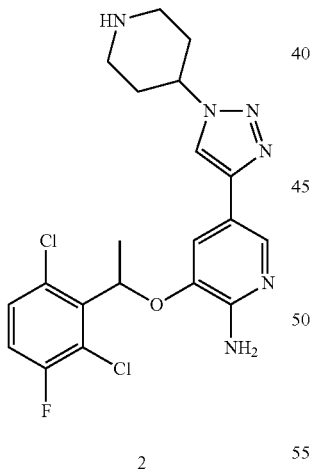

2

The product of the above mentioned Example 1 3-(1-(2,6-dichloro-3-fluorophenyl)ethoxy)-5-(1-(1-tert-butyl formatepiperidin-4-yl)-1H-1,2,3-triazol-4-yl)-2-aminopyridine (3.2 g, 5.8 mmol) was dissolved in dichloromethane (20 mL), trifluoroacetic acid (10 mL) was added, stirred for 2 h at room temperature. After the majority of the solvent was removed under reduced pressure, to the resultant mixture was added ethyl acetate (20 mL), and the reaction mixture was neutralized to pH=8-9 using saturated sodium bicarbonate solution under the cooling of ice water bath, meanwhile a light yellow solid was formed, filtered, and the filter cake was washed with a small amount of ethyl acetate to yield 2.2 g of the target product as light yellow solid. ¹H-NMR (DMSO, 400 MHz): δ 8.51 (s, 1H), 7.97 (s, 1H), 7.57-7.60 (m, 1H), 7.47 (t, 1H), 7.39 (s, 1H), 6.17 (d, 1H), 4.79-4.83 (m, 1H), 3.09-3.16 (m, 2H), 2.66-2.67 (m, 2H), 2.29-2.33 (m, 2H), 2.13-2.19 (m, 2H), 1.84 (d, 3H).

ESI (+) m/z: 451

Example 3

The synthesis of 3-(1-(2,6-dichloro-3-fluorophenyl)ethoxy)-5-(1-(1-benzylpiperidin-4-yl)-1H-1,2,3-triazol-4-yl)-2-aminopyridine (Compound 3)

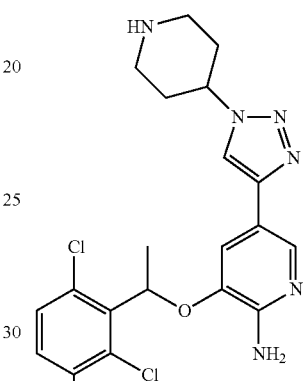

2

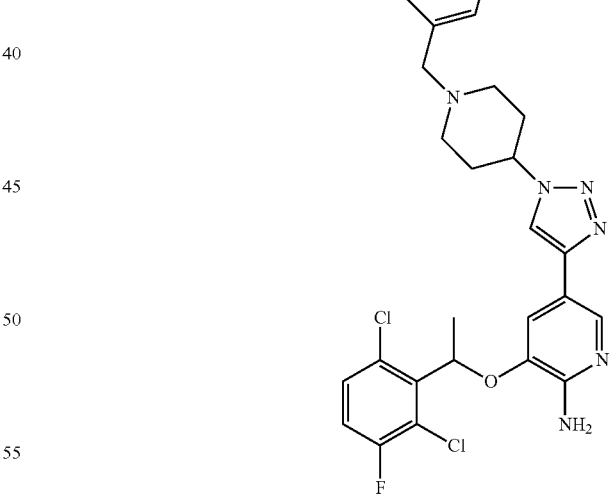

3

The product of the above mentioned Example 2 3-(1-(2,6-dichloro-3-fluorophenyl)ethoxy)-5-(1-(piperidin-4-yl)-1H-1,2,3-triazol-4-yl)-2-aminopyridine (451 mg, 1 mmol) was added to N,N-dimethyl formamide (10 mL), and to which were added potassium carbonate (276 mg, 2 mmol) and benzyl bromide (342 mg, 2 mmol). The reaction mixture was warmed to 90° C. for 5 h. After the reaction mixture was cooled to room temperature, to which was added water. The reaction mixture was extracted with dichloromethane, the organic layer was washed with water for several times, dried over anhydrous sodium sulfate, and then filtered, the filtrate was rotatedly concentrated to dryness to yield a solid, which was purified via silica gel column chromatography (dichloromethane:methanol=10:1) to yield the title compound as gray solid powder.

$^1$H NMR (CDCl-d$_3$, 400 Hz): δ 8.02 (s, 1H), 7.64 (s, 1H), 7.47 (s, 1H), 7.28-7.35 (m, 6H), 7.08 (t, 1H), 6.18 (q, 1H), 5.10 (br, 2H), 4.50-4.54 (m, 1H), 3.10-3.16 (m, 2H), 2.66-2.67 (m, 2H), 2.22-2.29 (m, 2H), 2.13-2.19 (m, 2H), 1.88 (d, 3H).

ESI (+) m/z: 541

Example 4

The synthesis of 3-(1-(2,6-dichloro-3-fluorophenyl)ethoxy)-5-(1-(1-p-cyanobenzoylpiperidin-4-yl)-1H-1,2,3-triazol-4-yl)-2-aminopyridine (Compound 4)

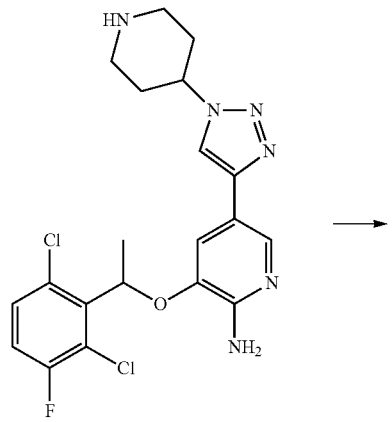

2

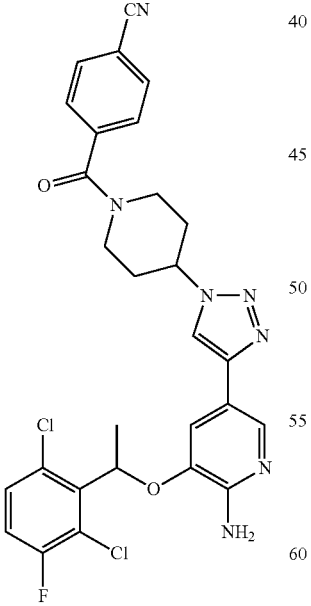

4

The product of the above mentioned Example 2 3-(1-(2,6-dichloro-3-fluorophenyl)ethoxy)-5-(1-(piperidin-4-yl)-1H-1,2,3-triazol-4-yl)-2-aminopyridine (451 mg, 1 mmol) was added to N,N-dimethyl formamide (10 mL), triethylamine (404 mg, 4 mmol) and p-cyanobenzoyl chloride (496.5 mg, 3 mmol) were added, and the reaction was performed overnight at room temperature. The resultant mixture was washed with water for several times, dried over anhydrous sodium sulfate, filtered, the filtrate was rotatedly concentrated to dryness to yield a solid, which was purified via silica gel column chromatography (dichloromethane/methanol=15:1) to yield the target product as white solid powder.

$^1$H NMR (CDCl-d$_3$, 400 Hz): δ 7.96 (s, 1H), 7.78 (d, 2H), 7.66 (s, 1H), 7.56 (d, 2H), 7.42 (s, 1H), 7.28 (m, 1H), 7.08 (t, 1H), 6.15 (q, 1H), 4.52-4.56 (m, 1H), 3.12-3.16 (m, 2H), 2.60-2.66 (m, 2H), 2.28-2.30 (m, 2H), 2.13-2.18 (m, 2H), 1.90 (d, 3H).

ESI (+) m/z: 580

Example 5

The synthesis of 3-(1-(2,6-dichloro-3-fluorophenyl)ethoxy)-5-(1-(1-p-fluorobenzoylpiperidin-4-yl)-1H-1,2,3-triazol-4-yl)-2-aminopyridine (Compound 5)

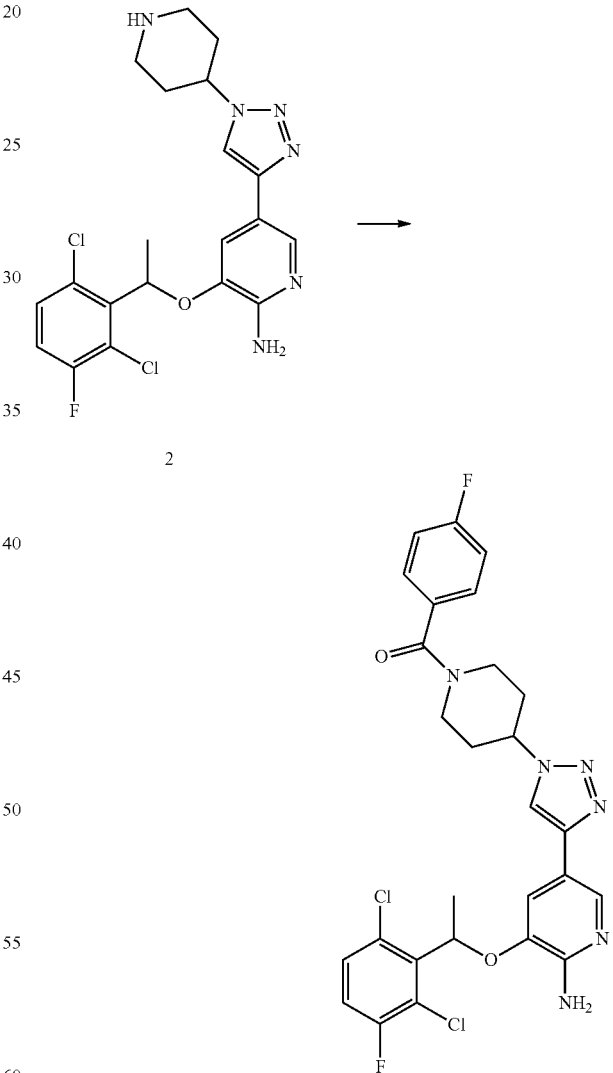

The product of the above mentioned Example 2 3-(1-(2,6-dichloro-3-fluorophenyl)ethoxy)-5-(1-(piperidin-4-yl)-1H-1,2,3-triazol-4-yl)-2-aminopyridine (451 mg, 1 mmol) was added to N,N-dimethyl formamide (10 mL), triethylamine (404 mg, 4 mmol) and p-fluorobenzoyl chloride (475.5 mg, 3 mmol) were added, and the reaction was performed overnight at room temperature. The resultant mixture was washed with water for several times, dried over anhydrous sodium sulfate, filtered, the filtrate was rotatedly concentrated to dryness to yield a solid, which was purified via silica gel column chromatography (dichloromethane/methanol=15:1) to yield the target product as white solid powder.

$^1$H NMR (CDCl-d$_3$, 400 Hz): δ 8.04 (s, 1H), 7.69 (s, 1H), 7.50 (d, 2H), 7.42 (s, 1H), 7.22-7.28 (m, 3H), 7.04 (t, 1H), 6.15 (q, 1H), 4.56-4.60 (m, 1H), 3.16-3.20 (m, 2H), 2.60-2.64 (m, 2H), 2.28-2.33 (m, 2H), 2.15-2.19 (m, 2H), 1.90 (d, 3H).

ESI (+) m/z: 573

Example 6

The synthesis of 3-(1-(2,6-dichloro-3-fluorophenyl)ethoxy)-5-(1-(1-p-tosylpiperidin-4-yl)-1H-1,2,3-triazol-4-yl)-2-aminopyridine (Compound 6)

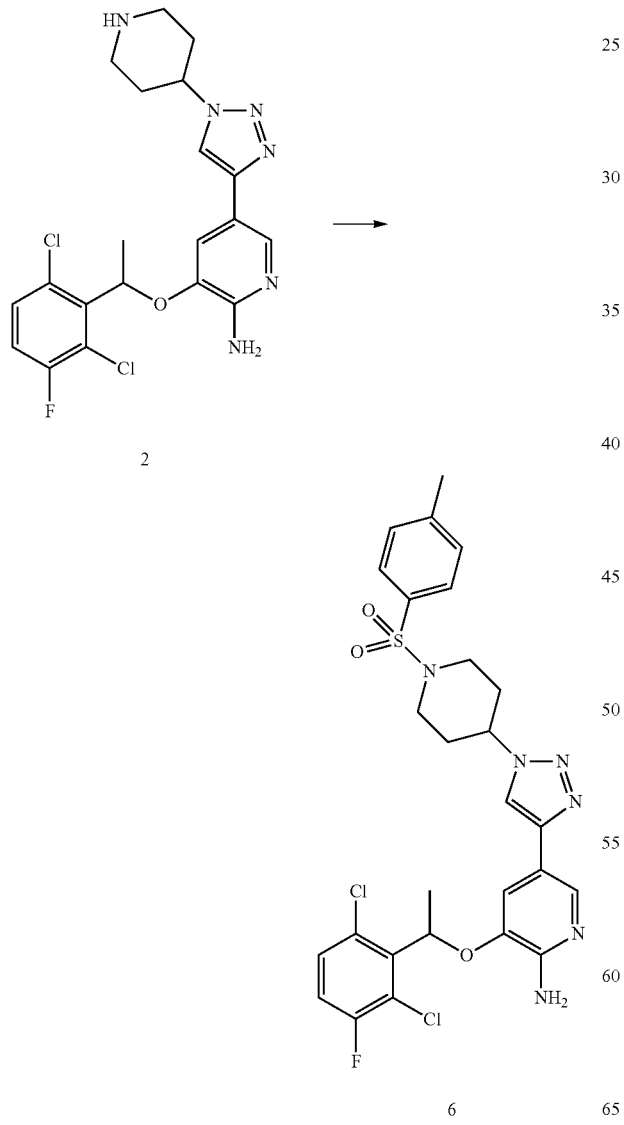

The product of the above mentioned Example 2 3-(1-(2,6-dichloro-3-fluorophenyl)ethoxy)-5-(1-(piperidin-4-yl)-1H-1,2,3-triazol-4-yl)-2-aminopyridine (451 mg, 1 mmol) was added to N,N-dimethyl formamide (10 mL), triethylamine (404 mg, 4 mmol) and p-toluenesulfonyl chloride (572 mg, 3 mmol) were added, and the reaction was performed overnight at room temperature. The resultant mixture was washed with water for several times, dried over anhydrous sodium sulfate, filtered, the filtrate was rotatedly concentrated to dryness to yield a solid, which was purified via silica gel column chromatography (dichloromethane/methanol=15:1) to yield the target product as white solid powder.

$^1$H NMR (CDCl-d$_3$, 400 Hz): δ 8.02 (s, 1H), 7.74 (d, 2H), 7.54 (s, 1H), 7.43 (m, 3H), 7.38 (s, 1H), 7.08 (t, 1H), 6.20 (q, 1H), 4.46-4.50 (m, 1H), 3.84-3.88 (m, 2H), 2.46-2.54 (m, 2H), 2.27-2.33 (m, 2H), 2.12-2.18 (m, 2H), 1.90 (d, 3H).

ESI (+) m/z: 605

Example 7

The synthesis of 3-(1-(2,6-dichloro-3-fluorophenyl)ethoxy)-5-(1-(1-mesylpiperidin-4-yl)-1H-1,2,3-triazol-4-yl)-2-aminopyridine (Compound 7)

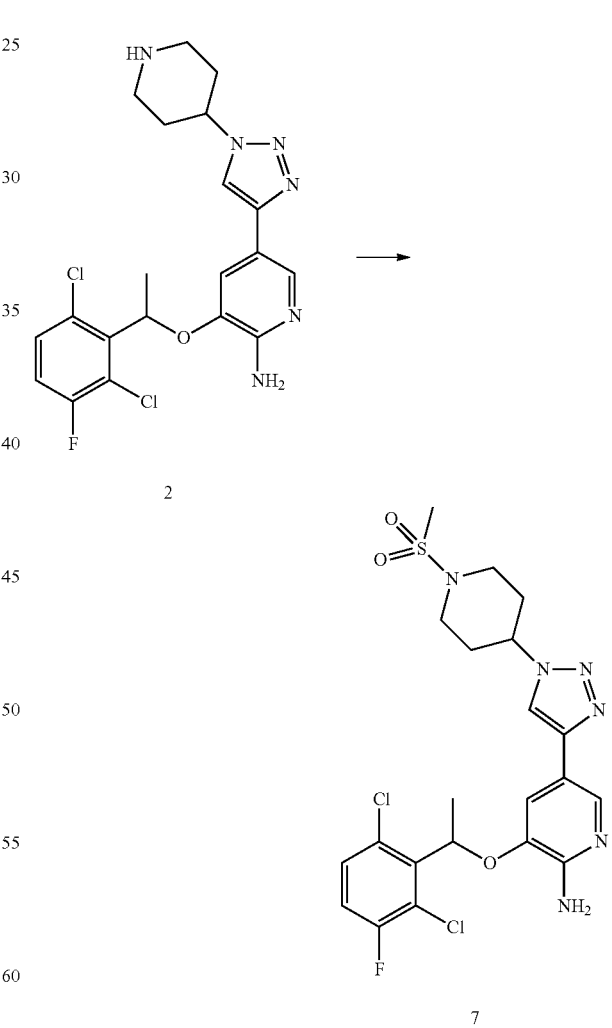

The product of the above mentioned Example 2 3-(1-(2,6-dichloro-3-fluorophenyl)ethoxy)-5-(1-(piperidin-4-yl)-1H-1,2,3-triazol-4-yl)-2-aminopyridine (451 mg, 1 mmol) was added to N,N-dimethyl formamide (10 mL), triethylamine (404 mg, 4 mmol) and methylsulfonyl chloride (343.6 mg, 3 mmol) were added, and the reaction was performed overnight at room temperature. The resultant mixture was washed with water for several times, dried over anhydrous sodium sulfate, filtered, the filtrate was rotately concentrated to dryness to yield a solid, which was purified via silica gel column chromatography (dichloromethane/methanol=20:1) to yield the target product as white solid powder.

$^1$H-NMR (DMSO-d$_6$, 400 MHz): δ 8.47 (s, 1H), 7.88 (s, 1H), 7.57-7.60 (m, 1H), 7.40-7.45 (m, 1H), 7.32 (s, 1H), 6.20 (d, 1H), 4.70-4.76 (m, 1H), 3.10-3.16 (m, 2H), 2.88 (s, 3H), 2.70-2.75 (m, 2H), 2.25-2.30 (m, 2H), 2.16-2.12 (m, 2H), 1.97 (d, 3H).

ESI (+) m/z: 529

Example 8

The synthesis of 3-(1-(2,6-dichloro-3-fluorophenyl)ethoxy)-5-(1-(1-methylpiperidin-4-yl)-1H-1,2,3-triazol-4-yl)-2-aminopyridine (Compound 8)

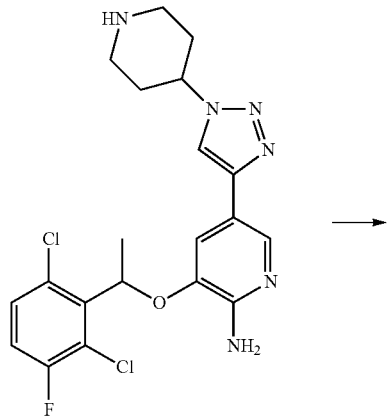

3-(1-(2,6-dichloro-3-fluorophenyl)ethoxy)-5-(1-(piperidin-4-yl)-1H-1,2,3-triazol-4-yl)-2-aminopyridine (451 mg, 1 mmol) in the above mentioned Example 2 was added to N,N-dimethyl formamide (10 mL), potassium carbonate (276 mg, 2 mmol) and iodomethane (425.7 mg, 3 mmol) were added, and the reaction was performed overnight at room temperature. The resultant mixture was washed with water for several times, dried over anhydrous sodium sulfate, filtered, the filtrate was rotately concentrated to dryness to yield a solid, which was purified via silica gel column chromatography (dichloromethane/methanol=10:1) to yield the target product as white solid powder.

$^1$H NMR (DMSO-d$_6$, 400 Hz): δ 8.45 (s, 1H), 7.80 (s, 1H), 7.60-7.64 (m, 1H), 7.42-7.46 (m, 1H), 7.30 (s, 1H), 6.13 (d, 1H), 4.66-4.70 (m, 1H), 3.13-3.17 (m, 2H), 2.66-2.72 (m, 2H), 2.34 (s, 3H), 2.20-2.34 (m, 2H), 2.16-2.12 (m, 2H), 1.96 (d, 3H).

ESI (+) m/z: 465

Example 9

The synthesis of 3-(1-(2,6-dichloro-3-fluorophenyl)ethoxy)-5-(1-((1-diphenylmethyl)azetidin-3-yl)-1H-1,2,3-triazol-4-yl)-2-aminopyridine (Compound 9)

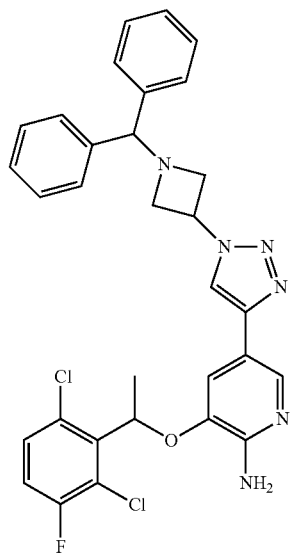

The title compound was prepared by the following steps.

1) The synthesis of 1-(diphenylmethyl)-3-azidoazetidine

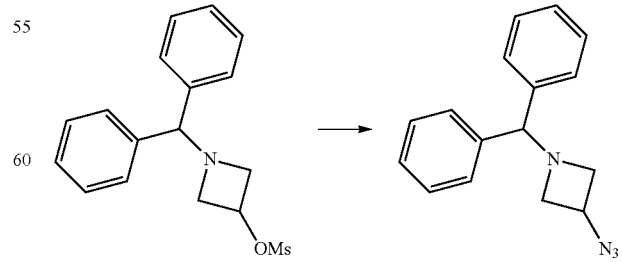

1-(diphenylmethyl)-3-hydroxyazetidine (5.5 g, 22.98 mmol) was dissolved in acetonitrile (16.5 mL), triethylamine (3.48 g, 34.45 mmol) was added. The reaction mixture was cooled to −10° C., methylsulfonyl chloride (3.16 g, 27.59 mmol) was added dropwise slowly. After completion of dropwise addition, the reaction was performed at 0° C. for 1 h, The resultant reaction liquid was poured into water, extracted with ethyl acetate. The organic layer was dried over anhydrous sodium sulfate, filtered, the filtrate was rotatedly concentrated to dryness to yield a white solid. The resultant white solid was added to N,N-dimethyl formamide (25 mL), sodium azide (5.38 g, 82.73 mmol) was added. The reaction mixture was warmed to 100° C. and the reaction was performed overnight. The resultant reaction liquid was cooled to room temperature, poured into water, extracted with dichloromethane. The organic phase was washed with water, dried over anhydrous sodium sulfate, filtered; the filtrate was rotatedly concentrated to dryness to yield 1-(diphenylmethyl)-3-azidoazetidine.

2) The synthesis of 3-(1-(2,6-dichloro-3-fluorophenyl)ethoxy)-5-(1-(1-(diphenylmethyl)azetidin-3-yl)-1H-1,2,3-triazol-4-yl)-2-aminopyridine The compound 3-(1-(2,6-dichloro-3-fluorophenyl)ethoxy)-5-ethynyl-2-aminopyridine (4.2 g, 12.62 mmol) was dissolved in methanol (40 mL), and diisopropylethylamine (8.36 g, 64.78 mmol), copper iodide (62 mg, 0.33 mmol) and 1-(diphenylmethyl)-3-azidoazetidine (3.34 g, 12.62 mmol) were added successively. The reaction was stirred overnight at room temperature. TLC test showed that the raw materials were completely reacted. The resultant mixture was concentrated under reduced pressure;
the residue was purified via silica gel column chromatography (dichloromethane/methanol=20:1) to yield the target product as gray solid powder.
¹H NMR (CDCl-d₃, 400 Hz): δ 8.14 (s, 1H), 7.96 (s, 1H), 7.44-7.52 (m, 4H), 7.36 (s, 1H), 7.21-7.33 (m, 7H), 7.08 (t, 1H), 6.20 (q, 1H), 5.22-5.28 (m, 1H), 5.0 (brs, 2H), 4.56 (s, 1H), 3.70-3.74 (m, 2H), 3.52-3.60 (m, 2H), 1.96 (d, 3H).
ESI (+) m/z: 589

Example 10

The synthesis of 3-(1-(2,6-dichloro-3-fluorophenyl)ethoxy)-5-(1-(azetidin-3-yl)-1H-1,2,3-triazol-4-yl)-2-aminopyridine (Compound 10)

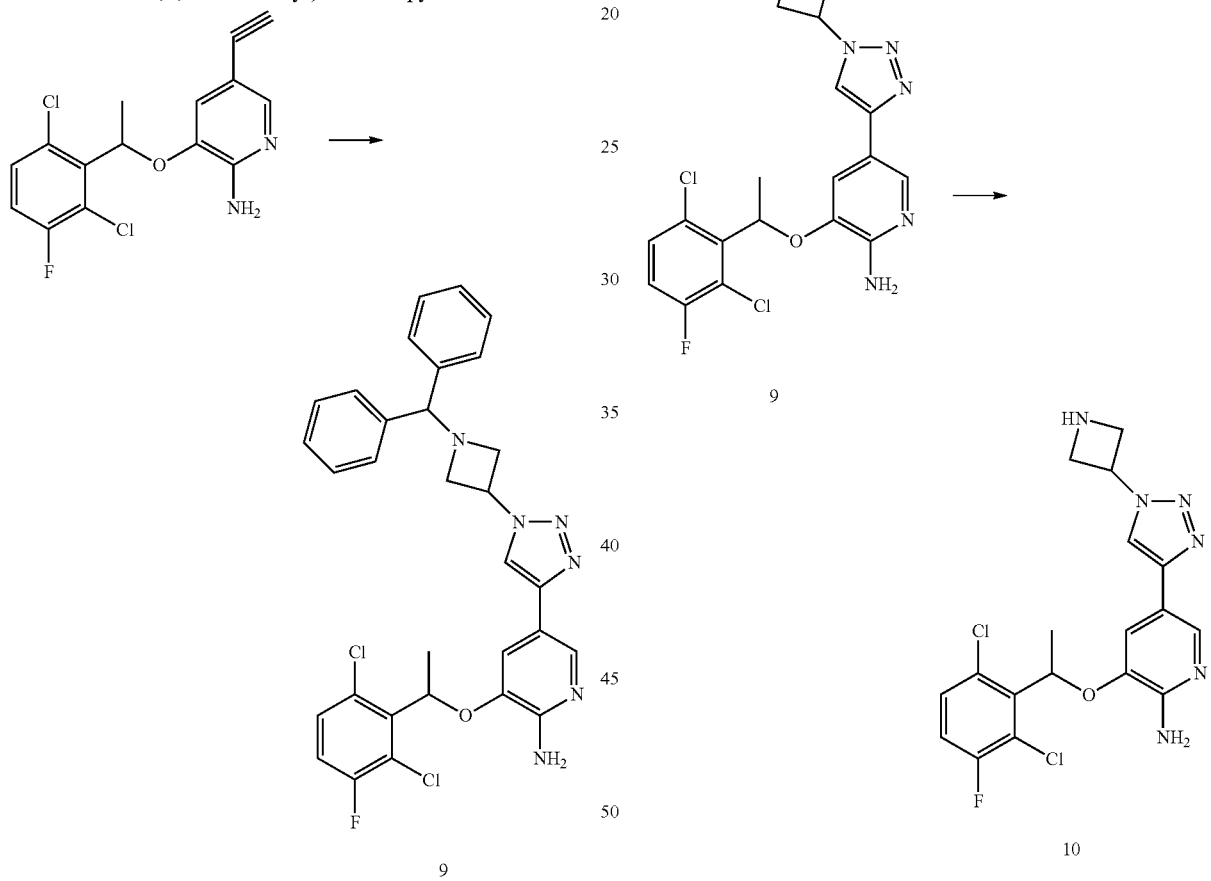

The product of the above mentioned Example 9 3-(1-(2,6-dichloro-3-fluorophenyl)ethoxy)-5-(1-(1-(diphenylmethyl)azetidin-3-yl)-1H-1,2,3-triazol-4-yl)-2-aminopyridine (2.2 g, 3.73 mmol) was dissolved in methanol (40 mL), and palladium hydroxide/carbon (220 mg) was added to perform the hydrogenation reaction. TLC test showed that the raw materials were completely reacted. After filtration, the filtrate was concentrated under reduced pressure to yield the target product as white solid powder.
¹H NMR (CDCl-d₃, 400 Hz): δ 8.24 (s, 1H), 8.07 (s, 1H), 7.44-7.50 (m, 1H), 7.36 (s, 1H), 7.14 (t, 1H), 6.14 (q, 1H), 5.24-5.27 (m, 1H), 3.63-3.70 (m, 2H), 3.46-3.54 (m, 2H), 1.98 (d, 3H).
ESI (+) m/z: 423

Example 11

The synthesis of (S)—N-tert-butyloxycarbonyl-(4-(6-amino-5-(1-(2,6-dichloro-3-fluorophenyl)ethoxy)pyridin-3-yl)-1H-1,2,3-triazol-1-yl) piperidine (Compound 11)

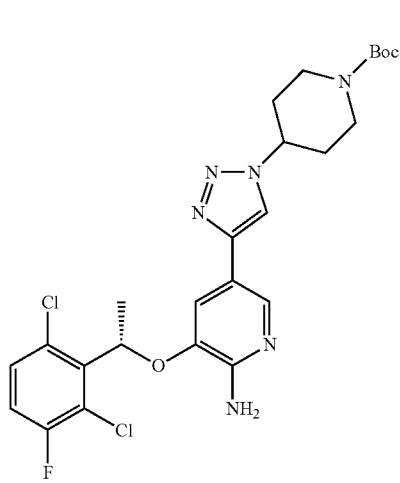

The title compound was prepared by the following steps.

1) The synthesis of (S)-3-(1-(2,6-dichloro-3-fluorophenyl)ethoxy)-2-nitropyridine

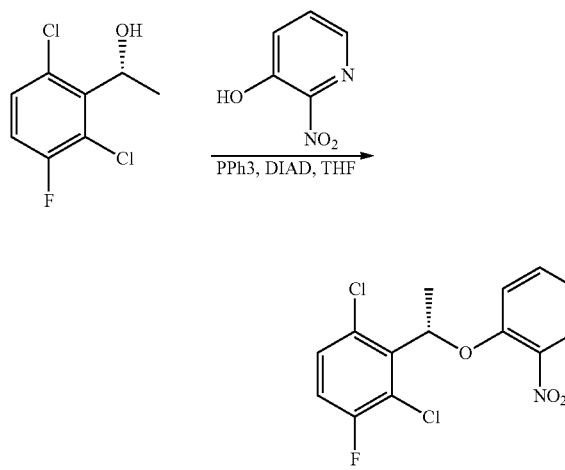

The compound (R)-1-(2,6-dichloro-3-fluorophenyl)ethanol (12 g, 57.42 mmol) was dissolved in tetrahydrofuran (110 mL), 2-nitro-3-hydroxypyridine (8.84 g, 63.16 mmol) and triphenylphosphine (21.06 g, 80.39 mmol) were added, and the reaction mixture was stirred for 1 h at room temperature. Diisopropyl azodicarboxylate (16.26 g, 80.39 m mol) was added dropwise under the cooling of ice bath. The temperature of the reaction liquid was raised to 30° C., and the reaction was stirred overnight. After TLC test has showed that reaction was completed, the reaction liquid was concentrated under reduced pressure; the resultant residue was purified via silica gel column chromatography (petroleum ether:ethyl acetate=5:1) to yield the target product as yellow solid (15.2 g, yield: 80%).

2) The synthesis of (S)-3-(1-(2,6-dichloro-3-fluorophenyl)ethoxy)-2-aminopyridine

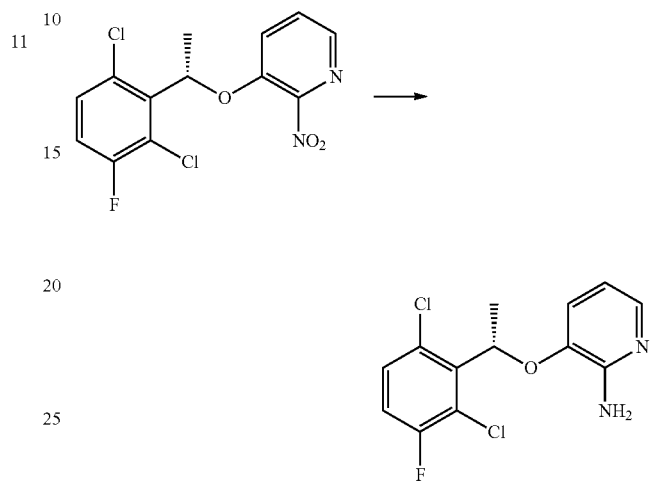

The compound (S)-3-(1-(2,6-dichloro-3-fluorophenyl)ethoxy)-2-nitropyridine (15.2 g, 45.9 mmol) was suspended in ethanol (150 mL), and palladium/carbon was added to perform the hydrogenation reaction. TLC test showed that the raw materials were completely reacted. The reaction liquid was filtered; the filtrate was concentrated under reduced pressure to remove ethanol to yield (S)-3-(1-(2,6-dichloro-3-fluorophenyl)ethoxy)-2-aminopyridine (12 g, yield: 87%).

3) The synthesis of (S)-5-bromo-3-(1-(2,6-dichloro-3-fluorophenyl)ethoxy)-2-aminopyridine

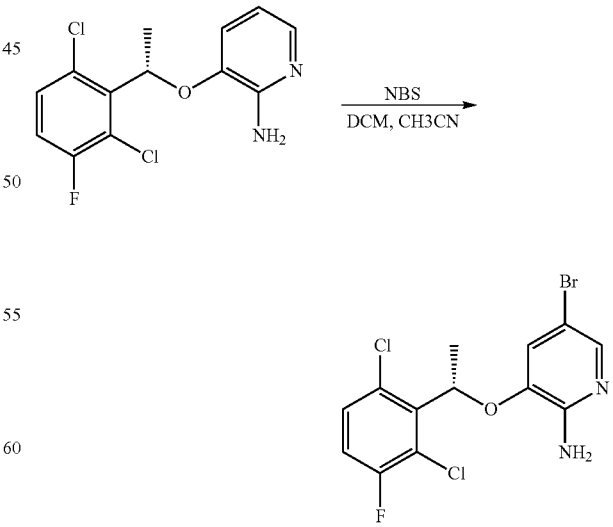

(S)-3-(1-(2,6-dichloro-3-fluorophenyl)ethoxy)-2-aminopyridine (12 g, 39.87 mmol) was dissolved in dichloromethane (15 mL), a solution of N-bromosuccimide (7.1 g, 39.87 m mol) in acetonitrile (20 mL) was added dropwise slowly under the cooling of ice bath, and the reaction was stirred. After TLC test has showed that reaction was completed, a small amount of NaHSO₃ solution was added to quench it, and the pH was adjusted to about 8-9 using sodium carbonate solution. The mixed solution was concentrated under reduced pressure to remove dichloromethane and acetonitrile. The residue was extracted with dichloromethane, and the organic layer was separated, washed with water, dried over anhydrous sodium sulfate, concentrated; the residue was purified via silica gel column chromatography (petroleum ether:ethyl acetate=4:1) to yield the target product as yellow solid (12.5 g, yield: 83%).

4) The synthesis of (S)-3-(1-(2,6-dichloro-3-fluorophenyl)ethoxy)-5-(2-(trimethylsilyl)ethynyl)-2-aminopyridine

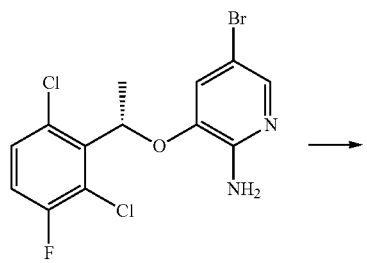

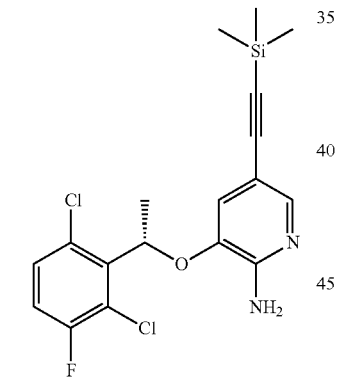

The compound (S)-5-bromo-3-(1-(2,6-dichloro-3-fluorophenyl)ethoxy)-2-aminopyridine (12.58 g, 33.11 mmol) was dispersed in toluene (100 mL), and triethylamine (14.05 g, 139.06 mmol) and copper iodide (126 mg, 0.66 mmol) were added successively. Under the protection of N₂ atmosphere, PdCl₂(PPh₃)₂ (465 mg, 0.66 mmol) was added. The reaction mixture was heated to 30° C., stirred for 0.5 h. Ethynyltrimethylsilane (9.11 g, 92.71 mmol) was added dropwise, gradually warmed to 90° C., and stirred overnight. Through HPLC test, it was found that the raw materials were completely reacted. The reaction liquid was cooled down, washed with water, and the toluene layers were combined. The toluene layer was dried over anhydrous Na₂SO₄, concentrated; the residue was purified via silica gel column chromatography (petroleum ether:ethyl acetate=3:1) to yield the target product as yellow solid (10.6 g, yield: 80%).

5) The synthesis of (S)-3-(1-(2,6-dichloro-3-fluorophenyl)ethoxy)-5-ethynyl-2-aminopyridine

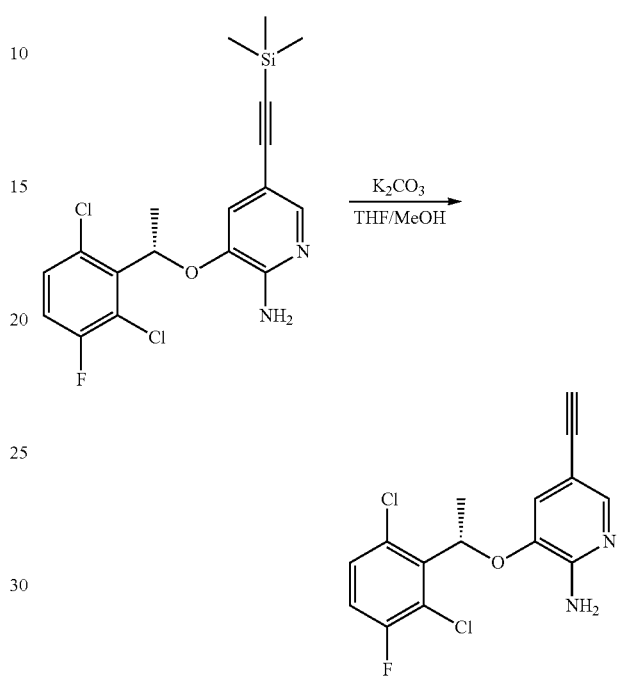

(S)-3-(1-(2,6-dichloro-3-fluorophenyl)ethoxy)-5-(2-(trimethylsilyl)ethynyl)-2-aminopyridine (10.6 g, 26.7 mmol) was dissolved in methanol (50 mL), potassium carbonate (7.38 g, 53.4 mmol) was added, and the reaction was stirred overnight at room temperature. TLC test showed that the raw materials were completely reacted. The reaction liquid was concentrated under reduced pressure, extracted with ethyl acetate; the organic layer was washed with water and saturated sodium chloride solution successively, dried over anhydrous sodium sulfate, concentrated; the residue was purified via silica gel column chromatography [petroleum ether:ethyl acetate=3:1 (v:v)] to yield the target product as yellow solid (8.2 g, yield: 94%).

6) The synthesis of (S)—N-tert-butyloxycarbonyl-(4-(6-amino-5-(1-(2,6-dichloro-3-fluorop henyl)ethoxy) pyridin-3-yl)-1H-1,2,3-triazol-1-yl)piperidine

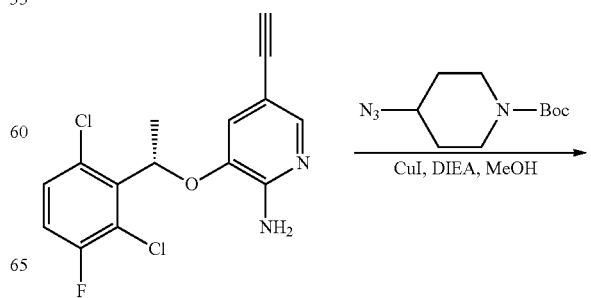

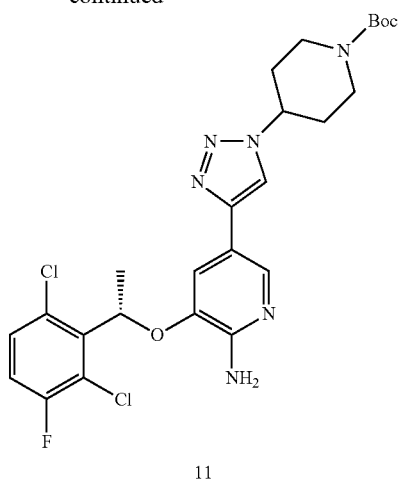

11

The compound (S)-3-(1-(2,6-dichloro-3-fluorophenyl)ethoxy)-5-ethynyl-2-aminopyridine (8.2 g, 25.23 mmol) was dissolved in methanol (80 mL), diisopropylethylamine (16.71 g, 129.55 mmol), copper iodide (123 mg, 0.65 mmol) and N-Boc-4-azidopiperidine (as oily matter) were added successively, and the reaction was stirred overnight at room temperature. TLC test showed that the raw materials were completely reacted. The reaction liquid was concentrated under reduced pressure; the residue was purified via silica gel column chromatography (dichloromethane/methanol=20:1) to yield the target product as gray solid powder (2.5 g, yield: 20%).

ESI (+) m/z: 551

Example 12

The synthesis of (S)-3-(1-(2,6-dichloro-3-fluorophenylethoxy)-5-(1-(piperidin-4-yl)-1H-1,2,3-triazol-4-yl)-2-aminopyridine (Compound 12)

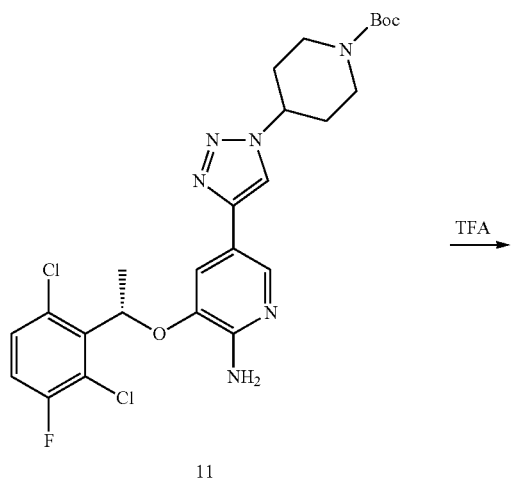

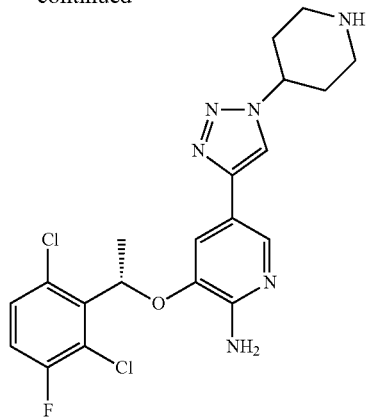

12

The product of Example 11 (S)-3-(1-(2,6-dichloro-3-fluorophenylethoxy)-5-(1-(piperidin-4-yl)-1H-1,2,3-triazol-4-yl)-2-aminopyridine (1 g, 1.81 mmol) was suspended in dichloromethane (5 mL), and trifluoroacetic acid (5 mL) was added dropwise under the cooling of ice bath, and the reaction was stirred at room temperature. After 2 h, TLC test showed that the raw materials were completely reacted. The reaction liquid was concentrated under reduced pressure to remove the majority of solvent, dichloromethane (10 mL) was added, and the pH was neutralized to pH=8-9 using saturated sodium carbonate solution under the cooling of ice bath. The resultant mixture was extracted with the mixed solution of dichloromethane/methanol (V:V=10:1); the organic layer was washed with water for several times, dried over anhydrous sodium sulfate, filtered, the filtrate was rotatedly concentrated to dryness to yield a solid, which was washed with ethyl acetate for several times to yield the target product 12 as solid (450 mg, yield: 52%).

$^1$H NMR (DMSO-d$_6$, 400 MHz): δ 8.36 (m, 1H), 7.94 (m, 1H), 7.54-7.56 (m, 1H), 7.42-7.46 (m, 1H), 7.23-7.24 (m, 1H), 6.04-6.09 (m, 1H), 5.88-5.89 (m, 1H), 4.46-4.57 (m, 1H), 3.05-3.08 (m, 2H), 2.61-2.67 (m, 2H), 2.01-2.05 (m, 2H), 1.79-1.88 (m, 5H).

ESI (+) m/z: 451

Example 13

The synthesis of (R)-3-(1-(2,6-dichloro-3-fluorophenyl)ethoxy)-5-(1-(piperidin-4-yl)-1H-1,2,3-triazol-4-yl)-2-aminopyridine (Compound 13)

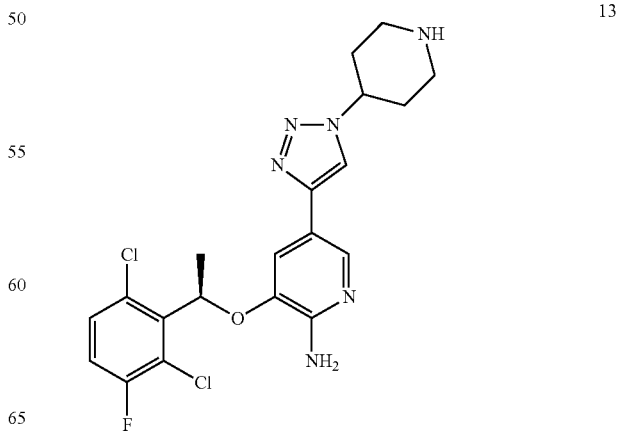

According to the method of the above mentioned Example 11, (R)-1-(2,6-dichloro-3-fluorophenyl)ethanol was replaced with (S)-1-(2,6-dichloro-3-fluorophenyl)ethanol to yield the title compound.

$^1$H NMR (DMSO-$d_6$, 400 MHz): δ 8.36 (m, 1H), 7.97 (m, 1H), 7.56-7.58 (m, 1H), 7.42-7.46 (m, 1H), 7.23-7.25 (m, 1H), 6.04-6.09 (m, 1H), 5.88-5.89 (m, 1H), 4.48-4.58 (m, 1H), 3.05-3.08 (m, 2H), 2.63-2.67 (m, 2H), 2.0-2.05 (m, 2H), 1.79-1.88 (m, 5H).

ESI (+) m/z: 451

II. Preparation Example of the Preparation of the Compounds of the Present Invention

Example 14

Preparation of Capsules

| | |
|---|---|
| Compound 2 | 20 g |
| starch | 140 g |
| microcrystalline cellulose | 65 g |

According to the conventional method, the above mentioned materials were mixed uniformly and then filled into common gelatin capsules to yield 1000 capsules.

According to similar methods, the capsules containing other Example compounds were prepared respectively.

III. Examples of Activity Test of the Compounds of the Present Invention

Test Example 1

The Inhibitory Effect of the Compounds of the Present Invention Against the Proliferation of Human Breast Cancer Cells (MDA-MB-231)

The human breast cancer cells in the logarithmic phase were inoculated to 96-well culture plates (180 μl/well) at a density of about 5500/well. The well for each concentration was triplicated. Solvent control wells of corresponding concentrations and apoptosis-free wells were also established. After adherent growth for 24 hr, the compounds of the present invention were added at 20 μl/well, and the cells were cultured for 72 hr under the conditions of 10% Hyclone fetal calf serum, 37° C., 5% $CO_2$. 50 ul of 50% cold trichloroacetic acid (TCA) was added, and was placed at 4° C. for 1 h to fix the cells. The liquid was decanted, gently washed with distilled water for 5 times, and air dried. 4 mg/ml SRB solution prepared by 1% glacial acetic acid was added at 100 μl/well so as to stain for 15 min at room temperature. The supernatant was discarded, and the residue was washed with 1% acetic acid for 5 times and air dried. To each well was added 150 μl of 10 mM Tris solution (pH 10.5) to dissolve the conjugated SRB. The OD value was measured at a wavelength of 510 nm using a Microplate Reader, and the $IC_{50}$ value of the compound of the present invention against MDA-MB-231 cells was calculated as:

| Compound | $IC_{50}$ (μM) |
|---|---|
| The compound of Example 2 | 9.53 |

The results of the test showed that: the compounds of the present invention have favourable proliferation inhibitory effect against human breast cancer cells (MDA-MB-231).

Test Example 2

The Inhibitory Effect of the Compounds of the Present Invention Against the Proliferation of Human Colon Cancer Cells (HT-29)

According to the experimental method of Test Example 1, the $IC_{50}$ value of the compound of the present invention against HT-29 cells was calculated as:

| Compound | $IC_{50}$ (μM) |
|---|---|
| The compound of Example 2 | 5.26 |

The results of the test showed that: the compounds of the present invention have favourable proliferation inhibitory effect against human colon cancer cells (HT-29).

Test Example 3

The Inhibitory Effect of the Compounds of the Present Invention Against the Proliferation of Human Lung Cancer Cells (H1975)

According to the experimental method of Test Example 1, the $IC_{50}$ value of the compound of the present invention against H1975 cells was calculated as:

| Compound | $IC_{50}$ (μM) |
|---|---|
| The compound of Example 2 | 11.66 |

The results of the test showed that: the compounds of the present invention have favourable proliferation inhibitory effect against human lung cancer cells (H1975).

Test Example 4

The Western Blot Test

The human lung cancer cells (H1975) in the logarithmic phase were inoculated to 6-well culture plates at a density of about 4×10$^5$/well. The cells were adherently grown for 24 hr. Four wells were selected, wherein two wells were added with the compound of Example 2 respectively (1 μM/well and 5 μM/well). The other two wells were not added with drugs. The cells were cultured for 6 hr under the conditions of 10% Hyclone fetal calf serum, 37° C., 5% $CO_2$. EGF was added to the above two wells and one of the drug-free well to stimulate for 15 min. After the cells were washed with cold PBS, sample loading buffer (2×SDS Lysis Buffer+1M DTT+$H_2O$) was added to lyse the cells. The lysate of the cells was heated for 10 min at 100° C., centrifuged for 5 min at 12000 g, and the supernatant was took out. The supernatant was subjected to SDS-PAGE electrophoretic analysis. At 25 mA constant current, after wetly transferred for 2 h, the proteins were transferred to PVDF (polyvinylidine difluoride) membrane. The PVDF membrane was took out, incubated with the corresponding primary antibody (pMet) at 4° C. overnight. After washing with TBST for 3 times under oscillation (10 min for each time), the corresponding secondary antibody (HRP-labeled Goat Anti-Rabbit IgG (H+L)) was added and incubated for 1 h at room temperature. After washing with TBST for 3 times, images were developed with ECL luminescence kit, and were mounted. Actin protein was used as the Loading Control. The results for the test is shown in FIG. 1.

The results of the test showed that: human lung cancer cells (H1975) initiates the downstream signal pathway under the induction of EGF, and the compound of Example 2 can effectively inhibit the phosphorylation of c-Met receptor at the concentration of 1 μM and 5 μM.

Test Example 5

The Inhibitory Effect Against the Growth of Subcutaneously Transplanted Tumors of Human Lung Cancer H1975 in Nude Mice The inhibitory effect of compound of Example 2 of the present invention against subcutaneously transplanted tumors of human lung cancer H1975 in nude mice and the intensity thereof were observed.

Solvent: 0.5% sodium carboxymethylcellulose (0.5% CMC-Na).

The compound of Example 2 was dispersed in 0.5% CMC-Na.

Three test groups were established, which were: 0.5% CMC-Na solvent control group, the groups of the compound of Example 2 at 250 mg/kg and 125 mg/kg, respectively.

Experimental animals: BALB/cA nude mice, female, 5 weeks old, body weight 18±2 g. 4 mice for each group.

Experimental method: human lung cancer H1975 cell strain (5×10$^6$/each mouse) was inoculated to nude mice subcutaneously at the side of the body thereof. The diameter of subcutaneously transplanted tumors in nude mice was measured by a vernier caliper. After the tumors had grown to 100 mm$^3$, the animals were divided into groups randomly. The compound of Example 2 were administered by intragastric administration according to the above two dosages, and solvent control groups were administered with equal amount of solvent by intragastric administration, wherein the administration was performed once daily for a continuous 14 days. During the entire experimental process, the diameter of transplanted tumors was measured every two weeks, and the body weight of the mice was measured simultaneously so as to observe if toxic reactions were occurred.

The computational formula of tumor volume (Tumor, TV) is: TV=½×a×b$^2$, wherein a and b denote length and width respectively.

Figure 2:
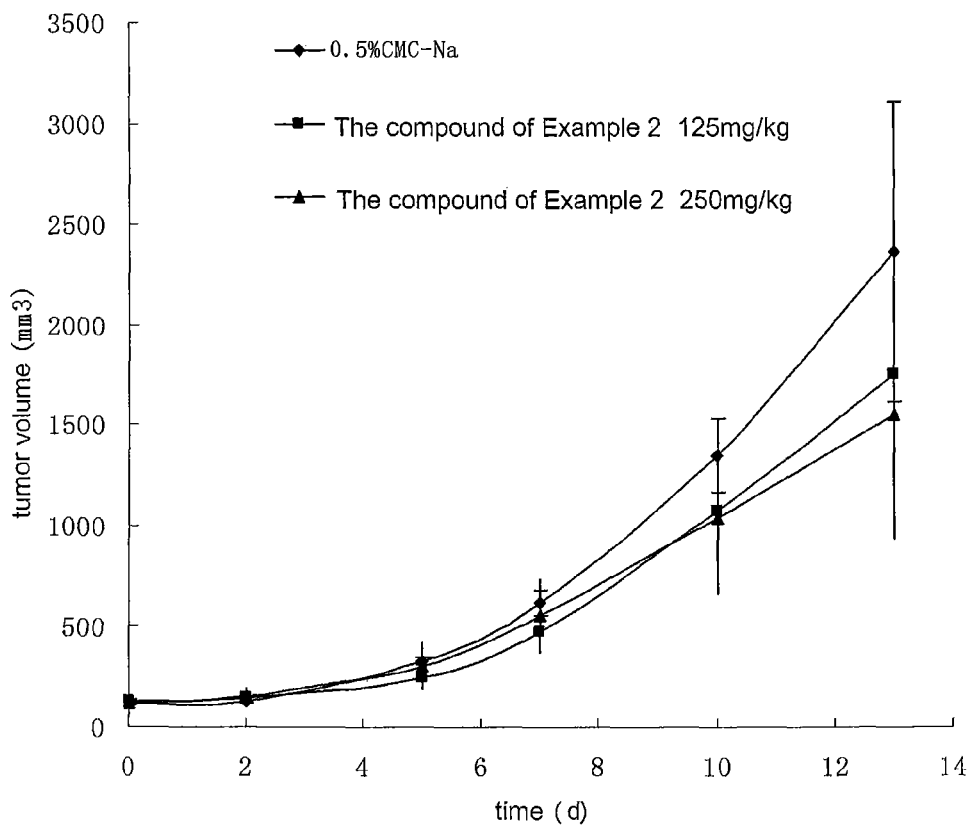
FIG. 2 is the tumor growth curve of human lung cancer H1975 bearing mice for different administration dosages of the compound of Example 2.
Figure 3:
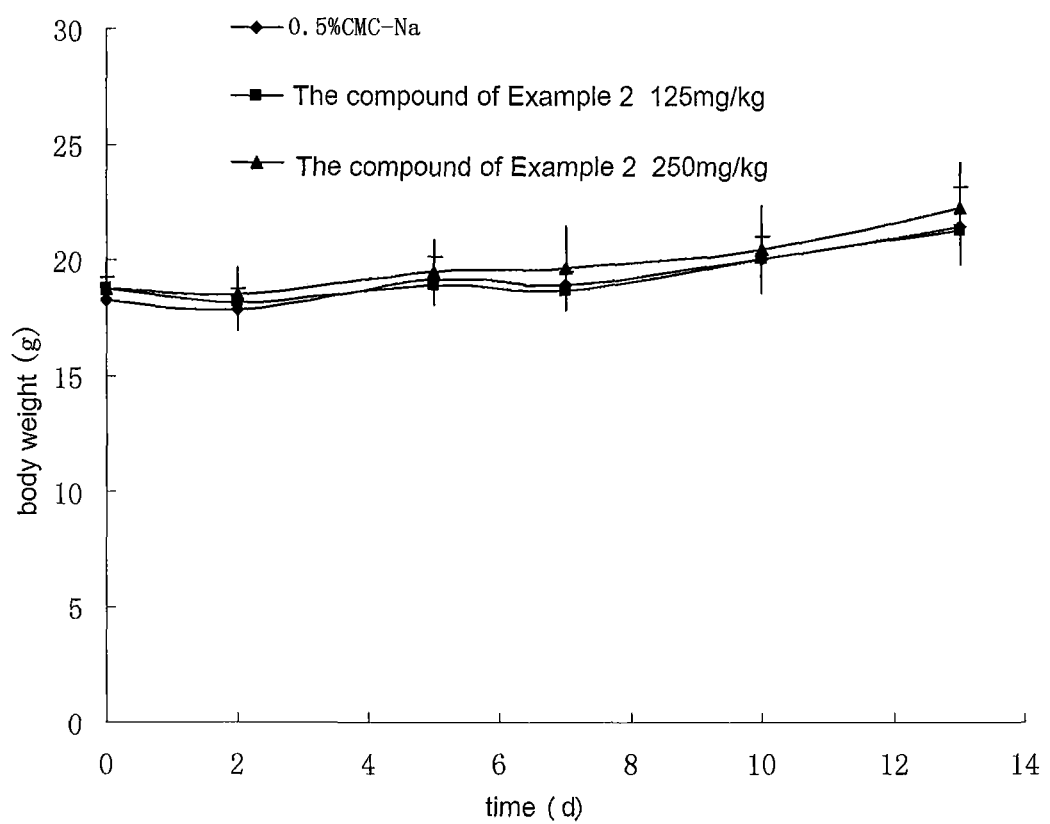
FIG. 3 is the body weight growth curve of human lung cancer H1975 bearing mice for different administration dosages of the compound of Example 2.

The tumor growth curves of the three experimental groups are shown in FIG. 2, and the body weight growth curves thereof are shown in FIG. 3. The results showed that the compounds of the present invention have favorable inhibitory effect against the growth of subcutaneously transplanted tumors of human lung cancer H1975 in nude mice and showed good safety.

Test Example 6

Enzyme Linked Immunosorbant Assay (1) The enzyme reaction substrate Poly(Glu, Tyr) 4:1 was diluted to 20 μg/mL, 1254/well coated enzyme label plate with potassium ion-free PBS (10 mM sodium phosphate buffer, 150 mM NaCl, pH7.2-7.4), which was placed at 37° C. to allow to react for 12-16 h. The liquid in the wells was discarded. The plate was washed with 200 μL/well of T-PBS (potassium ion-free PBS containing 0.1% Tween-20) for three times (each for 5 min). The enzyme label plate was placed into a drying oven at 37° C. to dry for 1-2 h.

(2) To each well was added 504 of ATP solution diluted with reaction buffer (50 mM HEPES pH 7.4, 50 mM MgCl$_2$, 0.5 mM MnCl$_2$, 0.2 mM Na$_3$VO$_4$, 1 mM DTT), and to each well was added 1 μL of the compounds. When adding the test compounds, 6 concentration gradients were set for each compound (the starting concentrations and dilution times were determined according to the results of preliminary screening so as to ensure that the maximum inhibition ratio was about 80% and the minimum inhibition ratio was about 20%, and more than two concentration points were in the vicinity of 50% inhibition ratio), and then 504 of c-Met kinase domain recombination protein diluted with reaction buffer was added to initiate the reaction. Two ATP-free control wells were needed for each of the experiments. The reaction was placed on a shaking table at 37° C. (100 rpm) for 1 h. The liquid in the wells was discarded and the plate was washed with T-PBS for three times.

(3) The antibody PY99 was added at 1004/well (the antibody was diluted with T-PBS containing BSA (5 mg/mL) in 1:500). The reaction was performed on a shaking table at 37° C. for 0.5 h. The liquid in the wells was discarded and the plate was washed with T-PBS for three times.

(4) The horseradish peroxidase-labeled goat anti-mouse secondary antibody was added at 100 μL/well (the antibody was diluted with T-PBS containing BSA (5 mg/mL) in 1:2000), The reaction was performed on a shaking table at 37° C. for 0.5 h. The liquid in the wells was discarded and the plate was washed with T-PBS for three times.

(5) 2 mg/ml of OPD colour developing solution (diluted with 0.1M citric acid-sodium citrate buffer (pH=5.4) containing 0.03% H$_2$O$_2$) was added at 1004/well, and the reaction was performed at 25° C. for 1-10 min under protection from light.

(6) 2M H$_2$SO$_4$ was added at 50 μL/well to terminate the reaction, and the values were read by a microplate reader VERSAmax with adjustable wavelength, wherein the wavelength was 490 nm. Through calculation, the inhibitory IC$_{50}$ values of the compounds of Example 2, 12 and 13 against the activity of receptor tyrosine kinase c-Met enzyme were obtained as:

| Compounds | Average inhibition ratio (%) | | | | | | IC$_{50}$ (nM) |
|---|---|---|---|---|---|---|---|
| (nM) | 200 | 66 | 22 | 7 | 2 | 0.8 | mean ± SD |
| The compound of Example 2 | 78.0 | 76.8 | 69.9 | 51.0 | 26.9 | 8.4 | 6.7 ± 2.3 |
| The compound of Example 12 | 77.5 | 76.3 | 61.7 | 39.8 | 18.2 | 7.9 | 11.7 ± 2.3 |
| The compound of Example 13 | 88.2 | 88.0 | 79.7 | 67.7 | 62.2 | 31.1 | 1.7 ± 0.4 |

The results of the test showed that: the compounds of the present invention have favorable inhibitory effect against the enzyme activity of receptor tyrosine kinase c-Met.

The applicant has completely illustrated the present invention in details. Apparently, upon reading the above mentioned contents of the present invention, a person skilled in the art can modify, change or amend the present invention without departing from the spirits of the present invention, and these equivalents are also within the scope as defined by the appended claims of the present application.

The invention claimed is:
1. A compound represented by the following general formula (I) or a pharmaceutically acceptable salt thereof,

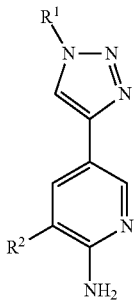
(I)

wherein:
$R^1$ is selected from H, $C_1$-$C_6$alkyl, $C_1$-$C_6$alkyl substituted by 1-3 halogen, $C_3$-$C_8$cycloalkyl, $C_3$-$C_8$cycloalkyl substituted by 1-3 halogen, —CONR'R", aryl, heteroaryl or nitrogen-containing saturated heterocyclyl;
$R^2$ is selected from —$OR^3$, —$SR^3$ or —$NR^3$, wherein $R^3$ is H, $C_1$-$C_6$alkyl, $C_1$-$C_6$alkyl substituted by 1-3 halogen, —(CR'R")$_{0-6}$-aryl, —(CR'R")$_{0-6}$-heteroaryl or —(CR'R")$_{0-6}$—nitrogen-containing saturated heterocyclyl; and wherein:
said aryl, heteroaryl and nitrogen-containing saturated heterocyclyl is unsubstituted or substituted by halogen, $C_1$-$C_6$alkyl, $C_1$-$C_6$alkyl substituted by aryl, $C_1$-$C_6$alkoxy, $C_3$-$C_8$cycloalkyl, —NR'R", —COR''', —COOR''', —SOOR''' or —OH;
said R' and R" are each independently H, $C_1$-$C_4$alkyl or $C_1$-$C_4$alkyl substituted by 1-3 halogen; and
said R''' is selected from the following groups: H, $C_1$-$C_4$alkyl, $C_1$-$C_4$alkyl substituted by 1-3 halogen, aryl that is unsubstituted or substituted by halogen, $C_1$-$C_4$alkyl, $C_1$-$C_4$alkoxy, —CN, —$NH_2$ or —OH and heteroaryl that is unsubstituted or substituted by—halogen, $C_1$-$C_4$alkyl, $C_1$-$C_4$alkoxy, —CN, —$NH_2$ or —OH.

2. A compound according to claim 1 or a pharmaceutically acceptable salt thereof, having the structure of the following formula (II):

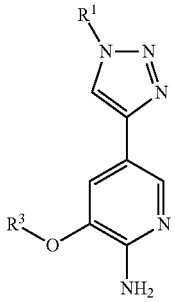
(II)

wherein $R^1$ and $R^3$ are as defined in claim 1.
3. The compound of formula (II) according to claim 2 or a pharmaceutically acceptable salt thereof, wherein $R^3$ is —(CR'R")$_{0-4}$-aryl or —(CR'R")$_{0-4}$-heteroaryl, said aryl or heteroaryl is unsubstituted or substituted by halogen, $C_1$-$C_4$alkyl or $C_1$-$C_4$alkoxy, said R' and R" are each independently H, $C_1$-$C_4$alkyl or $C_1$-$C_4$alkyl substituted by 1-3 halogen.

4. The compound of formula (II) according to claim 3 or a pharmaceutically acceptable salt thereof, wherein $R^3$ is —(CR'R")$_{1-2}$-aryl, said aryl is unsubstituted or substituted by halogen or $C_1$-$C_4$alkyl, said R' and R" are each independently H or —$C_1$-$C_4$alkyl.

5. The compound of formula (II) according to claim 4 or a pharmaceutically acceptable salt thereof, wherein $R^3$ is —(CR'R")-phenyl, said phenyl is substituted by halogen, said R' and R" are each independently H or methyl.

6. The compound of formula (II) according to claim 5 or a pharmaceutically acceptable salt thereof, wherein $R^3$ is —(CR'R")-phenyl, said phenyl is substituted by halogen, said R', R" are each independently H or methyl in (S) or (R) configuration.

7. The compound of formula (II) according to claim 3 or a pharmaceutically acceptable salt thereof, wherein $R^1$ is aryl, heteroaryl or nitrogen-containing saturated heterocyclyl, wherein said aryl, heteroaryl or nitrogen-containing saturated heterocyclyl is unsubstituted or substituted by halogen, $C_1$-$C_6$alkyl, $C_1$-$C_4$alkyl substituted by aryl, $C_1$-$C_6$alkoxy, $C_3$-$C_8$cycloalkyl, —$NH_2$, —COR''', —COOR''', —SOOR''' or —OH; said R''' is H, $C_1$-$C_4$alkyl, $C_1$-$C_4$alkyl substituted by 1-3 halogen, aryl that is unsubstituted or substituted by halogen, $C_1$-$C_4$alkyl, $C_1$-$C_4$alkoxy, —CN, —$NH_2$ or —OH, or heteroaryl that is unsubstituted or substituted by halogen, $C_1$-$C_4$alkyl, $C_1$-$C_4$alkoxy, —CN, —$NH_2$ or —OH.

8. The compound according to claim 7 or a pharmaceutically acceptable salt thereof, wherein $R^1$ is nitrogen-containing saturated heterocyclyl, said nitrogen-containing saturated heterocyclyl is unsubstituted or substituted by halogen, $C_1$-$C_6$alkyl, $C_1$-$C_2$alkyl substituted by aryl, $C_1$-$C_6$alkoxy, —$NH_2$, —COR''', —COOR''', —SOOR''' or —OH; said R''' is H, $C_1$-$C_4$alkyl, $C_1$-$C_4$alkyl substituted by 1-3 halogen, aryl that is unsubstituted or substituted by halogen, $C_1$-$C_4$alkyl, $C_1$-$C_4$alkoxy, —CN, —$NH_2$ or —OH, or heteroaryl that is unsubstituted or substituted by halogen, $C_1$-$C_4$alkyl, $C_1$-$C_4$alkoxy, —CN, —$NH_2$ or —OH.

9. The compound of formula (II) according to claim 8 or a pharmaceutically acceptable salt thereof, wherein $R^1$ is nitrogen-containing saturated heterocyclyl, said nitrogen-containing saturated heterocyclyl is unsubstituted or substituted by halogen, $C_1$-$C_4$alkyl, $C_1$-$C_2$alkyl substituted by phenyl, $C_1$-$C_4$alkoxy, —$NH_2$, —COR''', —COOR''', —SOOR''' or —OH; said R''' is H, $C_1$-$C_4$alkyl, $C_1$-$C_4$alkyl substituted by 1-3 halogen, aryl that is unsubstituted or substituted by halogen, $C_1$-$C_4$alkyl, $C_1$-$C_4$alkoxy, —CN, —$NH_2$ or —OH, or heteroaryl that is unsubstituted or substituted by halogen, $C_1$-$C_4$alkyl, $C_1$-$C_4$alkoxy, —CN, —$NH_2$ or —OH.

10. The compound of formula (II) according to claim 9 or a pharmaceutically acceptable salt thereof, wherein $R^1$ is piperidyl, pyrrolidinyl, pyrazolidinyl, azetidinyl or morpholinyl, wherein said piperidyl, pyrrolidinyl, pyrazolidinyl, azetidinyl and morpholinyl is unsubstituted or substituted by halogen, $C_1$-$C_4$alkyl, $C_1$-$C_4$alkyl substituted by aryl, $C_1$-$C_4$alkoxy, —COR''', —COOR''', —SOOR''', —$NH_2$ or —OH; said R''' is H, $C_1$-$C_4$alkyl, $C_1$-$C_4$alkyl substituted by 1-3 halogen, aryl that is unsubstituted or substituted by halogen, $C_1$-$C_4$alkyl, $C_1$-$C_4$alkoxy, —CN, —$NH_2$ or —OH, or heteroaryl that is unsubstituted or substituted by halogen, $C_1$-$C_4$alkyl, $C_1$-$C_4$alkoxy, —CN, —$NH_2$ or —OH.

11. The compound of formula (II) according to claim 10 or a pharmaceutically acceptable salt thereof, wherein $R^1$ is piperidyl, said piperidyl is unsubstituted or substituted by $C_1$-$C_4$alkyl, —COR''', —COOR''', —SOOR''' or $C_1$-$C_2$alkyl substituted by phenyl; said R'" is H, $C_1$-$C_4$alkyl, $C_1$-$C_4$alkyl substituted by 1-3 halogen, phenyl that is unsubstituted or substituted by halogen, $C_1$-$C_4$alkyl, $C_1$-$C_4$alkoxy, —CN, —$NH_2$ or —OH, thiazolyl that is unsubstituted or substituted by halogen, $C_1$-$C_4$alkyl, $C_1$-$C_4$alkoxy, —CN, —$NH_2$ or —OH, imidazolyl that is unsubstituted or substituted by halogen, $C_1$-$C_4$alkyl, $C_1$-$C_4$alkoxy, —CN, —$NH_2$ or —OH, pyridiyl that is unsubstituted or substituted by halogen, $C_1$-$C_4$alkyl, $C_1$-$C_4$alkoxy, —CN, —$NH_2$ or —OH, or pyrazinyl that is unsubstituted or substituted by halogen, $C_1$-$C_4$alkyl, $C_1$-$C_4$alkoxy, —CN, —$NH_2$ or —OH.

12. The compound of formula (II) according to claim 11 or a pharmaceutically acceptable salt thereof, wherein $R^1$ is piperidyl that is unsubstituted or substituted by $C_1$-$C_4$alkyl, $C_1$-$C_2$alkyl substituted by phenyl, —COR'", —COOR'" or —SOOR'", said R'" is $C_1$-$C_4$alkyl or phenyl substituted by halogen, $C_1$-$C_4$alkyl or —CN.

13. The compound according to claim 1 or a pharmaceutically acceptable salt thereof, said compound is selected from:
- 3-(1-(2,6-dichloro-3-fluorophenyl)ethoxy)-5-(1-(1-tert-butyl formatepiperidin-4-yl)-1H-1,2,3-triazol-4-yl)-2-aminopyridine;
- 3-(1-(2,6-dichloro-3-fluorophenyl)ethoxy)-5-(1-(piperidin-4-yl)-1H-1,2,3-triazol-4-yl)-2-aminopyridine;
- 3-(1-(2,6-dichloro-3-fluorophenyl)ethoxy)-5-(1-(1-benzylpiperidin-4-yl)-1H-1,2,3-triazol-4-yl)-2-aminopyridine;
- 3-(1-(2,6-dichloro-3-fluorophenyl)ethoxy)-5-(1-(1-p-cyanobenzoylpiperidin-4-yl)-1H-1,2,3-triazol-4-yl)-2-aminopyridine;
- 3-(1-(2,6-dichloro-3-fluorophenyl)ethoxy)-5-(1-(1-p-fluorobenzoylpiperidin-4-yl)-1H-1,2,3-triazol-4-yl)-2-aminopyridine;
- 3-(1-(2,6-dichloro-3-fluorophenyl)ethoxy)-5-(1-(1-p-tosylpiperidin-4-yl)-1H-1,2,3-triazol-4-yl)-2-aminopyridine;
- 3-(1-(2,6-dichloro-3-fluorophenyl)ethoxy)-5-(1-(1-mesylpiperidin-4-yl)-1H-1,2,3-triazol-4-yl)-2-aminopyridine;
- 3-(1-(2,6-dichloro-3-fluorophenyl)ethoxy)-5-(1-(1-methylpiperidin-4-yl)-1H-1,2,3-triazol-4-yl)-2-aminopyridine;
- 3-(1-(2,6-dichloro-3-fluorophenyl)ethoxy)-5-(1-((1-diphenylmethyl)azetidin-3-yl)-1H-1,2,3-triazol-4-yl)-2-aminopyridine;
- 3-(1-(2,6-dichloro-3-fluorophenyl)ethoxy)-5-(1-(azetidin-3-yl)-1H-1,2,3-triazol-4-yl)-2-aminopyridine;
- (S)—N-tert-butyloxycarbonyl-(4-(6-amino-5-(1-(2,6-dichloro-3-fluorophenyl)ethoxy)pyridin-3-yl)-1H-1,2,3-triazol-1-yl)piperidine;
- (S)-3-(1-(2,6-dichloro-3-fluorophenylethoxy)-5-(1-(piperidin-4-yl)-1H-1,2,3-triazol-4-yl)-2-aminopyridine; and
- (R)-3-(1-(2,6-dichloro-3-fluorophenyl)ethoxy)-5-(1-(piperidin-4-yl)-1H-1,2,3-triazol-4-yl)-2-aminopyridine.

14. A pharmaceutical composition containing the compound according to claim 1 or a pharmaceutically acceptable salt thereof and pharmaceutically acceptable carriers.

15. A method for treating a tumor, comprising administering to a subject in need thereof an effective amount of a compound according to claim 1.

16. A method for preparing the compound of formula (II) according to claim 2, including the steps of:

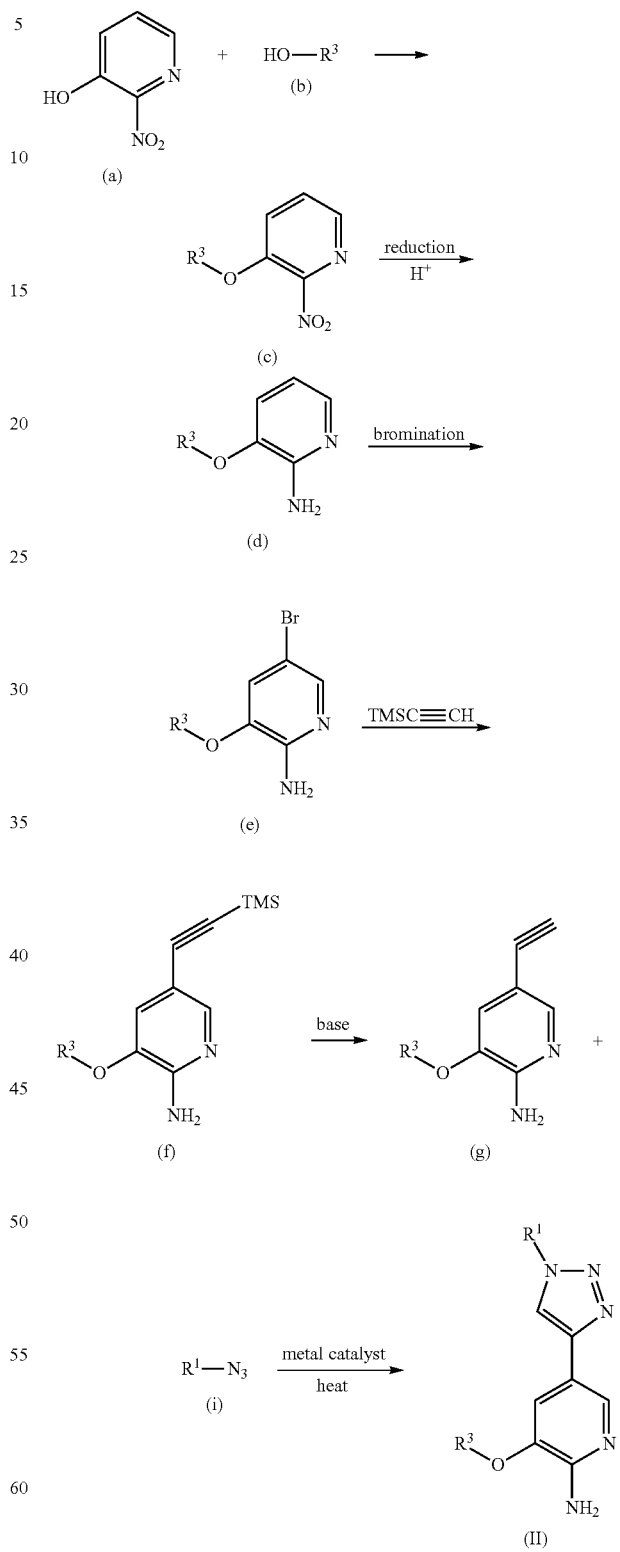

wherein $R^1$ and $R^3$ have the same meaning as those in claim 2;
3-hydroxy-2-nitropyridine, as the starting material, is reacted with compound (b) via nucleophilic substitution to yield compound (c); the compound (c) is converted to compound (e) via reduction, bromination; the compound (e) and trimethylsilylethyne are converted to compound (f) under the catalysis of a transition metal catalyst; the compound (f) is converted to compound (g) under the effect of a base; the compound (g) is reacted with organic azide (i) under the catalysis of a metal catalyst to yield the final product, i.e. the compound of general formula (II).

\* \* \* \* \*

UNITED STATES PATENT AND TRADEMARK OFFICE
CERTIFICATE OF CORRECTION

PATENT NO.        : 8,952,002 B2                                Page 1 of 1
APPLICATION NO.   : 14/372295
DATED             : February 10, 2015
INVENTOR(S)       : Luo It is certified that error appears in the above-identified patent and that said Letters Patent is hereby corrected as shown below:

In the Specification

Column 11, Lines 40-43: Please correct the formula below:

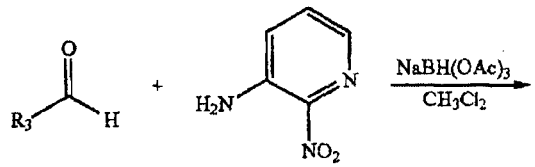

to read:

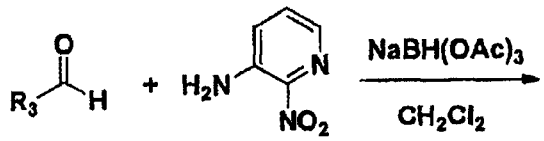

Column 39, Line 62: Please correct "1254/well" to read -- 125µL/well --

Signed and Sealed this
Eighth Day of September, 2015

Michelle K. Lee
*Director of the United States Patent and Trademark Office*